United States Patent
Green et al.

(10) Patent No.: US 6,693,108 B2
(45) Date of Patent: Feb. 17, 2004

(54) INHIBITORS OF C-JUN N TERMINAL KINASES (JNK) AND OTHER PROTEIN KINASES

(75) Inventors: Jeremy Green, Burlington, MA (US); Guy Bemis, Arlington, MA (US); Anne-Laure Grillot, Cambridge, MA (US); Mark Ledeboer, Acton, MA (US); Francesco G. Salituro, Marlboro, MA (US); Edmund Harrington, South Boston, MA (US); Huai Gao, Natick, MA (US); Christopher Baker, Bedford, MA (US); Jingrong Cao, Newton, MA (US); Michael Hale, Bedford, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 10/074,177

(22) Filed: Feb. 12, 2002

(65) Prior Publication Data

US 2003/0149051 A1 Aug. 7, 2003

Related U.S. Application Data

(63) Continuation of application No. PCT/US00/22445, filed on Aug. 11, 2000.
(60) Provisional application No. 60/211,517, filed on Jun. 14, 2000, provisional application No. 60/166,922, filed on Nov. 22, 1999, and provisional application No. 60/148,795, filed on Aug. 13, 1999.

(51) Int. Cl.[7] ................. C07D 401/04; C07D 405/04; C07D 403/04; C07D 413/04; A61K 31/341
(52) U.S. Cl. ........................................ 514/275; 544/331
(58) Field of Search ........................ 544/331; 514/275

(56) References Cited

U.S. PATENT DOCUMENTS

| | | | |
|---|---|---|---|
| 4,876,252 A | 10/1989 | Torley et al. | 514/224.8 |
| 5,356,897 A | 10/1994 | Oku et al. | 514/258 |

FOREIGN PATENT DOCUMENTS

| | | | |
|---|---|---|---|
| WO | WO 95/31541 | * | 11/1995 |
| WO | WO 98/52940 | * | 11/1998 |

OTHER PUBLICATIONS

Casanova et al., PubMed Abstract (Rev. Neurol. 28(9):909–15), May 1999.*
Traxler, Review: Oncologic, Endocrine & Metabolic. Protein tyrosine Kinase inhibitors in cancer treatment, Exp. Opin. Ther. Patents, 7(6):571–588, 1997.*
Damasio, Alzheimer's Disease and Related Dementias, Cecil Textbook of Medicine, 20th Edition, vol. 2, pp. 1992–6, 1996.*
Simone, Oncology: Introduction, Cecil Textbook of Medicine, 20th Edition, vol. 1, pp. 1004–1010, 1996.*
Layzer, Degenerative Diseases of the Nervous System, Cecil Textbook of Medicine, 20th Edition, vol. 2, pp. 2050–2057, 1996.*

Hassan et al, "Synthesis and reactions of 5-(D-arabino-tetrahydroxybutyl)-3-(2,3-dihydro-1,3,4-oxadiazole-2-thion-5-yl)-2-methylfuran and 5-(D-arabino-tetrahydroxybutyl)-3-(2-substituted amino-1,3,4-oxadiazol-5-yl)-2-methylfuran", Carbohydrate Research, 298: 123–126, 1997.

Paul et al, "Preparation of Subsituted N-Phenyl-4-aryl-2-pyrimidinamines as Mediator Release Inhibitors", J. Med. Chem., 36: 2716–2725, 1993.

Khisamutdinov et al, "Some reactions of 3-phenyl-5-methyl-4-isoxazole-carboxylic acid hydrazide", Khim. Fram. Zh., 2(8): 35–37, 1968.

Sokolov et al, "Isoxazole Compounds—(III) Synthesis of some isoxazolylazoles", Zhor. Obshchei Khim., 30: 1781–1787, 1960.

Ihle, N., and Krause, A., "Preparation of 4–Alkyl–2–[N–(tert–butoxycarbonyl)amino]–pyridines by Alkylation, Nucleophilic Addition, and Acylation of 2[N–(tert–butoxycarbonyl)amino]–4–picoline", J. Org. Chem., 61: 4810–4811, 1996.

* cited by examiner

Primary Examiner—Bruck Kifle
(74) Attorney, Agent, or Firm—Karoline K. M. Shair; Vertex Pharmaceuticals Incorporated

(57) ABSTRACT

The present invention provides compounds of formula I:

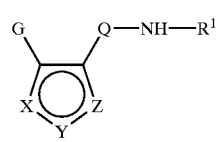

where $R^1$ is H, $CONH_2$, $T_{(n)}$—R, or $T_{(n)}$—$Ar^2$, n may be zero or one, and G, X, Y, Z, and Q are as described below. These compounds are inhibitors of protein kinase, particularly inhibitors of JNK, a mammalian protein kinase involved cell proliferation, cell death and response to extracellular stimuli. The invention also relates to methods for producing these inhibitors. The invention also provides pharmaceutical compositions comprising the inhibitors of the invention and methods of utilizing those compositions in the treatment and prevention of various disorders.

11 Claims, No Drawings

INHIBITORS OF C-JUN N TERMINAL KINASES (JNK) AND OTHER PROTEIN KINASES

This application is a continuation and claims the benefit, under 35 U.S.C. §365(c) and §120, of co-pending PCT International Application PCT/US00/22445 filed Aug. 11, 2000. PCT International Application PCT/US00/22445 was published under PCT Article 21(2) in English and claims priority under 35 U.S.C §119 to U.S. Provisional Application Ser. No. 60/148,795 filed Aug. 13, 1999, U.S. Provisional Application Ser. No. 60/166,922 filed Nov. 22, 1999, and U.S. Provisional Application Ser. No. 60/211,517 filed Jun. 14, 2000, and the entire contents of each of these applications are hereby incorporated by reference.

TECHNICAL FIELD OF INVENTION

The present invention relates to inhibitors of protein kinase, especially c-Jun N-terminal kinases (JNK), which are members of the mitogen-activated protein (MAP) kinase family. There are a number of different genes and isoforms which encode JNKS. Members of the JNK family regulate signal transduction in response to environmental stress and proinflammatory cytokines and have been implicated to have a role in mediating a number of different disorders. The invention also relates to methods f or producing these inhibitors. The invention also provides pharmaceutical compositions comprising the inhibitors of the invention and methods of utilizing those compositions in the treatment and prevention of various disorders.

BACKGROUND OF THE INVENTION

Mammalian cells respond to extracellular stimuli by activating signaling cascades that are mediated by members of the mitogen-activated protein (MAP) kinase family, which include the extracellular signal regulated kinases (ERKs), the p38 MAP kinases and the c-Jun N-terminal kinases (JNKs). MAP kinases (MAPKs) are activated by a variety of signals including growth factors, cytokines, UV radiation, and stress-inducing agents. MAPKs are serine/threonine kinases and their activation occur by dual phosphorylation of threonine and tyrosine at the Thr-X-Tyr segment in the activation loop. MAPKs phosphorylate various substrates including transcription factors, which in turn regulate the expression of specific sets of genes and thus mediate a specific response to the stimulus.

One particularly interesting kinase family are the c-Jun $NH_2$-terminal protein kinases, also known as JNKs. Three distinct genes, JNK1, JNK2, JNK3 have been identified and at least ten different splicing isoforms of JNKs exist in mammalian cells [Gupta et al., EMBO J., 15:2760–70 (1996)]. Members of the JNK family are activated by proinflammatory cytokines, such as tumor necrosis factor-α (TNFα) and interleukin-1 β (IL-1β), as well as by environmental stress, including anisomycin, UV irradiation, hypoxia, and osmotic shock [Minden et al., Biochemica et Biophysica Acta, 1333:F85–F104 (1997)].

The down-stream substrates of JNKs include transcription factors c-Jun, ATF-2, Elk1, p53 and a cell death domain protein (DENN) [Zhang et al. Proc. Natl. Acad. Sci. USA, 95:2586–91 (1998)]. Each JNK isoform binds to these substrates with different affinities, suggesting a regulation of signaling pathways by substrate specificity of different JNKs in vivo (Gupta et al., supra).

JNKs, along with other MAPKs, have been implicated in having a role in mediating cellular response to cancer, thrombin-induced platelet aggregation, immunodeficiency disorders, autoimmune diseases, cell death, allergies, osteoporosis and heart disease. The therapeutic targets related to activation of the JNK pathway include chronic myelogenous leukemia (CML), rheumatoid arthritis, asthma, osteoarthritis, ischemia, cancer and neurodegenerative diseases.

Several reports have detailed the importance of JNK activation associated with liver disease or episodes of hepatic ischemia [Nat. Genet. 21:326–9 (1999); FEBS Lett. 420:201–4 (1997);J. Clin. Invest. 102:1942–50 (1998); Hepatology 28:1022–30 (1998)]. Therefore, inhibitors of JNK may be useful to treat various hepatic disorders.

A role for JNK in cardiovascular disease such as myocardial infarction or congestive heart failure has also been reported as it has been shown JNK mediates hypertrophic responses to various forms of cardiac stress [Circ. Res. 83:167–78 (1998); Circulation 97:1731–7 (1998); J. Biol. Chem. 272:28050–6 (1997); Circ. Res. 79:162–73 (1996) ;Circ. Res. 78:947–53 (1996); J. Clin. Invest. 97:508–14 (1996)].

It has been demonstrated that the JNK cascade also plays a role in T-cell activation, including activation of the IL-2 promoter. Thus, inhibitors of JNK may have therapeutic value in altering pathologic immune responses [J. Immunol. 162:3176–87 (1999); Eur. J. Immunol. 28:3867–77 (1998); J. Exp. Med. 186:941–53 (1997); Eur. J. Immunol. 26:989–94 (1996)].

A role for JNK activation in various cancers has also been established, suggesting the potential use of JNK inhibitors in cancer. For example, constitutively activated JNK is associated with HTLV-1 mediated tumorigenesis [Oncogene 13:135–42 (1996)]. JNK may play a role in Kaposi's sarcoma (KS) because it is thought that the proliferative effects of bFGF and OSM on KS cells are mediated by their activation of the JNK signaling pathway [J. Clin. Invest. 99:1798–804 (1997)]. Other proliferative effects of other cytokines implicated in KS proliferation, such as vascular endothelial growth factor (VEGF), IL-6 and TNFα, may also be mediated by JNK. In addition, regulation of the c-jun gene in p210 BCR-ABL transformed cells corresponds with activity of JNK, suggesting a role for JNK inhibitors in the treatment for chronic myelogenous leukemia (CML) [Blood 92:2450–60 (1998)].

JNK1 and JNK2 are widely expressed in a variety of tissues. In contrast, JNK3 is selectively expressed in the brain and to a lesser extent in the heart and testis [Gupta et al., supra; Mohit et al., Neuron 14:67–78 (1995); Martin et al., Brain Res. Mol. Brain Res. 35:47–57 (1996)]. JNK3 has been linked to neuronal apoptosis induced by kainic acid, indicating a role of JNK in the pathogenesis of glutamate neurotoxicity. In the adult human brain, JNK3 expression is localized to a subpopulation of pyramidal neurons in the CA1, CA4 and subiculum regions of the hippocampus and layers 3 and 5 of the neocortex [Mohit et al., supra]. The CA1 neurons of patients with acute hypoxia showed strong nuclear JNK3-immunoreactivity compared to minimal, diffuse cytoplasmic staining of the hippocampal neurons from brain tissues of normal patients [Zhang et al., supra]. Thus, JNK3 appears to be involved involved in hypoxic and ischemic damage of CA1 neurons in the hippocampus.

In addition, JNK3 co-localizes immunochemically with neurons vulnerable in Alzheimer's disease [Mohit et al., supra]. Disruption of the JNK3 gene caused resistance of mice to the excitotoxic glutamate receptor agonist kainic acid, including the effects on seizure activity, AP-1 transcriptional activity and apoptosis of hippocampal neurons, indicating that the JNK3 signaling pathway is a critical component in the pathogenesis of glutamate neurotoxicity (Yang et al., *Nature,* 389:865–870 (1997)].

Based on these findings, JNK signalling, especially that of JNK3, has been implicated in the areas of apoptosis-driven neurodegenerative diseases such as Alzheimer's Disease, Parkinson's Disease, ALS (Amyotrophic Lateral Sclerosis), epilepsy and seizures, Huntington's Disease, traumatic brain injuries, as well as ischemic and hemorrhaging stroke.

There is a high unmet medical need to develop JNK specific inhibitors that are useful in treating the various conditions associated with JNK activation, especially considering the currently available, relatively inadequate treatment options for the majority of these conditions.

Recently, we have described crystallizable complexes of JNK protein and adenosine monophosphate, including complexes comprising JNK3, in U.S. Provisional Application No. 60/084,056, filed May 4, 1998. Such information has been extremely useful in identifying and designing potential inhibitors of various members of the JNK family, which, in turn, have the described above therapeutic utility.

Much work has been done to identify and develop drugs that inhibit MAPKs, such as p38 inhibitors. See, e.g., WO 98/27098 and WO 95/31451. However, to our knowledge, no MAPK inhibitors have been shown to be specifically selective for JNKs versus other related MAPKs.

Accordingly, there is still a great need to develop potent inhibitors at JNKs, including JNK3 inhibitors, that are useful in treating various conditions associated with JNK activation.

SUMMARY OF THE INVENTION

It has now been found that compounds of this invention and pharmaceutical compositions thereof are effective as inhibitors of c-Jun N-terminal kinases (JNK). These compounds have the general formula I:

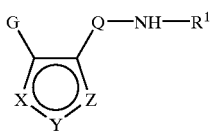

where $R^1$ is H, $CONH_2$, $T_{(n)}$—R, or $T_{(n)}$—$Ar^2$, n may be zero or one, and G, XYZ, and Q are as described below. Preferred compounds are those where the XYZ-containing ring is an isoxazole. Preferred G groups are optionally substituted phenyls and preferred Q are pyrimidine, pyridine or pyrazole rings.

These compounds and pharmaceutical compositions thereof are useful for treating or preventing a variety of disorders, such as heart disease, immunodeficiency disorders, inflammatory diseases, allergic diseases, autoimmune diseases, destructive bone disorders such as osteoporosis, proliferative disorders, infectious diseases and viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. The compositions are especially useful for disorders such as chronic myelogenous leukemia (CML), rheumatoid arthritis, asthma, osteoarthritis, ischemia, cancer, liver disease including hepatic ischemia, heart disease such as myocardial infarction and congestive heart failure, pathologic immune conditions involving T cell activation and neurodegenerative disorders.

DETAILED DESCRIPTION OF THE INVENTION

This invention provides novel compounds, and pharmaceutically acceptable derivatives thereof, that are useful as JNK inhibitors. These compounds have the general formula I:

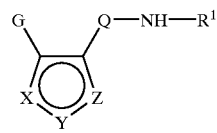

wherein:
X-Y-Z is selected from one of the following:

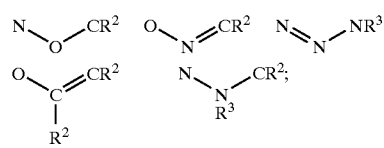

$R^1$ is H, $CONH_2$, $T_{(n)}$—R, or $T_{(n)}$—$Ar^2$;
R is an aliphatic or substituted aliphatic group;
n is zero or one;
T is C(=O), $CO_2$, CONH, $S(O)_2$, $S(O)_2NH$, $COCH_2$ or $CH_2$;
each $R^2$ is independently selected from hydrogen, —R, —$CH_2OR$, —$CH_2OH$, —CH=O, —$CH_2SR$, —$CH_2S$ $(O)_2R$, —$CH_2(C=O)R$, —$CH_2CO_2R$, —$CH_2CO_2H$, —$CH_2CN$, —$CH_2NHR$, —$CH_2N(R)_2$, —CH=N—OR, —CH=NNHR, —CH=NN(R)_2, —CH=NNHCOR, —CH=NNHCO_2R, —CH=NNHSO_2R, -aryl, -substituted aryl, —$CH_2$(aryl), —$CH_2$(substituted aryl), —$CH_2NH_2$, —$CH_2NHCOR$, —$CH_2NHCONHR$, —$CH_2NHCON(R)_2$, —$CH_2NRCOR$, —$CH_2NHCO_2R$, —$CH_2CONHR$, —$CH_2CON(R)_2$, —$CH_2SO_2NH_2$, —$CH_2$(heterocyclyl), —$CH_2$(substituted heterocyclyl), -(heterocyclyl), or -(substituted heterocyclyl);
each $R^3$ is independently selected from hydrogen, R, COR, $CO_2R$ or $S(O)_2R$;
G is R or $Ar^1$;
$Ar^1$ is aryl, substituted aryl, aralkyl, substituted aralkyl, heterocyclyl, or substituted heterocyclyl, wherein $Ar^1$ is optionally fused to a partially unsaturated or fully unsaturated five to seven membered ring containing zero to three heteroatoms;
Q—NH is

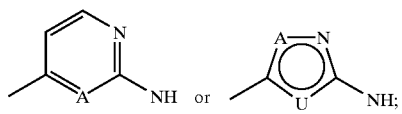

wherein the H of Q—NH is optionally replaced by $R^3$; A is N or $CR^3$;
U is $CR^3$, O, S, or $NR^3$;
$Ar^2$ is aryl, substituted aryl, heterocyclyl or substituted heterocyclyl, wherein $Ar^2$ is optionally fused to a partially unsaturated or fully unsaturated five to seven membered ring containing zero to three heteroatoms; and wherein each substitutable carbon atom in $Ar^2$, including the fused ring when present, is optionally and independently substituted by halo, R, OR, SR, OH, $NO_2$, CN, $NH_2$, NHR, $N(R)_2$, NHCOR, NHCONHR, $NHCON(R)_{21}$ NRCOR, $NHCO_2R$, $CO_2R$, $CO_2H$, COR, CONHR, $CON(R)_2$, $S(O)_2R$, $SONH_2$, $S(O)R$, $SO_2NHR$, or $NHS(O)_2R$, and wherein each saturated carbon in the fused ring is further optionally and independently substituted by =O, =S, =NNHR, =NNR$_2$, =N—OR, =NNHCOR, =NNHCO$_2$R, =NNHSO$_2$R, or =NR;

wherein each substitutable nitrogen atom in $Ar^2$ is optionally substituted by R, COR, $S(O)_2R$, or $CO_2R$.

As used herein, the following definitions shall apply unless otherwise indicated. The term "aliphatic" as used herein means straight chained, branched or cyclic $C_1$–$C_{12}$ hydrocarbons, preferably one to six carbons, which are completely saturated or which contain one or more units of unsaturation. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl. The term "alkyl" and "alkoxy" used alone or as part of a larger moiety refers to both straight and branched chains containing one to twelve carbon atoms. The terms "alkenyl" and "alkynyl" used alone or as part of a larger moiety shall include both straight and branched chains containing two to twelve carbon atoms. The terms "haloalkyl", "haloalkenyl" and "haloalkoxy" means alkyl, alkenyl or alkoxy, as the case may be, substituted with one or more halogen atoms. The term "halogen" means F, Cl, Br, or I. The term "heteroatom" means N, O or S and shall include any oxidized form of nitrogen and sulfur, and the quaternized form of any basic nitrogen.

The term "aryl", used alone or as part of a larger moiety as in "aralkyl", refers to aromatic ring groups having five to fourteen members, such as phenyl, benzyl, 1-naphthyl, 2-naphthyl, 1-anthracyl and 2-anthracyl, and heterocyclic aromatic groups or heteroaryl groups such as 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 3-pyridazinyl, 2-thiazolyl, 4-thiazolyl, 5-thiazolyl, 5-tetrazolyl, 2-triazolyl, 5-triazolyl, 2-thienyl, or 3-thienyl.

Aryl groups also include fused polycyclic aromatic ring systems in which a carbocyclic aromatic ring or heteroaryl ring is fused to one or more other rings. Examples include tetrahydronaphthyl, benzimidazolyl, benzothienyl, benzofuranyl, indolyl, quinolinyl, benzodiazepinyl, benzothiazolyl, benzooxazolyl, benzimidazolyl, isoquinolinyl, isoindolyl, acridinyl, benzoisoxazolyl, and the like. Also included within the scope of the term "aryl", as it is used herein, is a group in which one or more carbocyclic aromatic rings and/or heteroaryl rings are fused to a cycloalkyl or non-aromatic heterocyclyl, for example, indanyl or tetrahydrobenzopyranyl.

The term "heterocyclic ring" or "heterocyclyl" refers to a non-aromatic ring which includes one or more heteroatoms such as nitrogen, oxygen or sulfur in the ring. The ring can be five, six, seven or eight-membered and/or fused to another ring, such as a cycloalkyl or aromatic ring. Examples include 3-1H-benzimidazol-2-one, 3-1-alkyl-benzimidazol-2-one, 2-tetrahydrofuranyl, 3-tetrahydrofuranyl, 2-tetrahydropyranyl, 3-tetrahydropyranyl, 4-tetrahydropyranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxane, benzotriazol-1-yl, benzopyrrolidine, benzopiperidine, benzoxolane, benzothiolane, and benzothiane.

A compound of this invention may contain a ring that is fused to a partially saturated or fully unsaturated five to seven membered ring containing zero to three heteroatoms. Such a fused ring may be an aromatic or non-aromatic monocyclic ring, examples of which include the aryl and heterocyclic rings described above.

An aryl group (carbocyclic and heterocyclic) or an aralkyl group, such as benzyl or phenethyl, may contain one or more substituents. Examples of suitable substituents on the unsaturated carbon atom of an aryl group include a halogen, —R, —OR, —OH, —SH, —SR, protected OH (such as acyloxy), phenyl (Ph), substituted Ph, —OPh, substituted —OPh, —NO$_2$, —CN, —NH$_2$, —NHR, —N(R)$_2$, —NHCOR, —NHCONHR, —NHCON(R)$_2$, —NRCOR, —NHCO$_2$R, —CO$_2$R, —CO$_2$H, —COR, —CONHR, —CON(R)$_2$, —S(O)$_2$R, —SONH$_2$, —S(O)R, —SO$_2$NHR, or —NHS(O)$_2$ R, where R is an aliphatic group or a substituted aliphatic group.

An aliphatic group or a non-aromatic heterocyclic ring may contain one or more substituents. Examples of suitable substituents on the saturated carbon of an aliphatic group or of a non-aromatic heterocyclic ring include those listed above for the unsaturated carbon, such as in an aromatic ring, as well as the following: =O, =S, =NNHR, =NNR$_2$, =N—OR, =NNHCOR, =NNHCO$_2$R, =NNHSO$_2$R, or =NR.

A substitutable nitrogen on an aromatic or non-aromatic heterocyclic ring may be optionally substituted. Suitable substituents on the nitrogen include R, COR, S(O)$_2$R, and CO$_2$R, where R is an aliphatic group or a substituted aliphatic group.

Compounds derived by making isosteric or bioisosteric replacements of carboxylic acid or ester moieties of compounds described herein are within the scope of this invention. Isosteres, which result from the exchange of an atom or group of atoms to create a new compound with similar biological properties to the parent carboxylic acid or ester, are known in the art. The bioisosteric replacement may be physicochemically or topologically based. An example of an isosteric replacement for a carboxylic acid is CONHSO$_2$ (alkyl) such as CONHSO$_2$Me.

It will be apparent to one skilled in the art that certain compounds of this invention may exist in tautomeric forms or hydrated forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C-$ or $^{14}C-$ enriched carbon are within the scope of this invention. Such compounds are useful, for example, as analytical tools or probes in biological assays.

One embodiment of this invention relates to compounds of formula I where the XYZ-containing ring is an isoxazole, as shown by the general formula IA below:

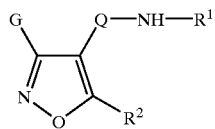
IA where $R^2$ is preferably alkyl, such as methyl, or $CH_2$ (heterocyclyl), such as $CH_2$(N-morpholinyl); G is preferably $Ar^1$; and $R^1$ is preferably $T_{(n)}-Ar^2$ or $T_{(n)}-R$, wherein n is most preferably zero. Most preferred are those compounds where G, $R^1$, and $R^2$ are as just described, and Q—NH is an aminopyridine or aminopyrimidine where the NH is at the 2 position of the ring:

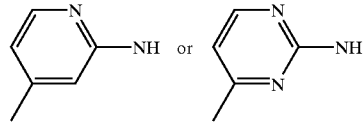

or Q—NH is an amino pyrazole:

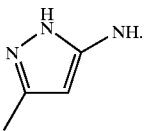

Table 1 below shows representative examples of IA compounds where Q is a pyrimidine, pyridine or pyrazole and $R^1$ is $Ar^2$, represented by formula IIA.

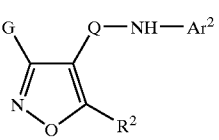
IIA

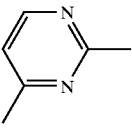
Q1

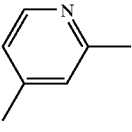
Q2

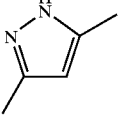
Q3

TABLE 1

Examples of Compounds of Formula IIA

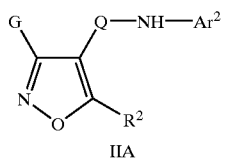
IIA

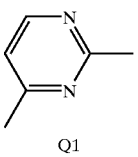 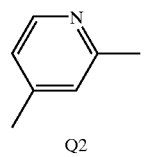 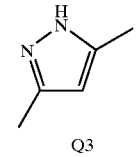
Q1  Q2  Q3

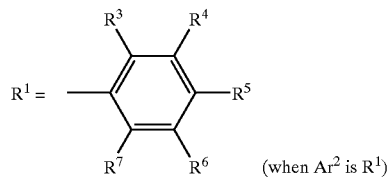

(when $Ar^2$ is $R^1$)

| No. | G | Q | $R^2$ | $R^3$ | $R^4$ | $R^5$ | $R^6$ | $R^7$ |
|---|---|---|---|---|---|---|---|---|
| IIA-1 | Ph | Q1 | Me | H | H | H | H | H |
| IIA-2 | Ph | Q1 | Me | H | H | OMe | H | H |

TABLE 1-continued

Examples of Compounds of Formula IIA

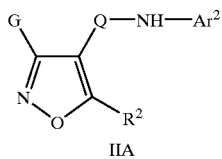

IIA

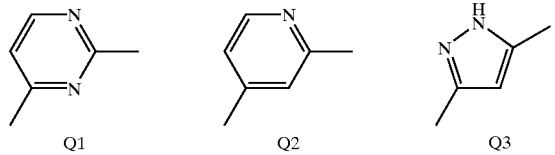

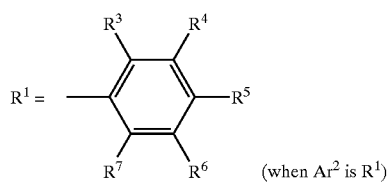

(when Ar² is R¹)

| No. | G | Q | R² | R³ | R⁴ | R⁵ | R⁶ | R⁷ |
|---|---|---|---|---|---|---|---|---|
| IIA-3 | Ph | Q1 | Me | H | OMe | OMe | H | H |
| IIA-4 | Ph | Q1 | Me | Me | H | H | H | H |
| IIA-5 | Ph | Q1 | Me | Me | H | CONH₂ | H | H |
| IIA-6 | Ph | Q1 | Me | Me | H | CN | H | H |
| IIA-7 | Ph | Q1 | Me | H | CN | H | H | H |
| IIA-8 | Ph | Q1 | Me | Me | F | H | H | H |
| IIA-9 | Ph | Q1 | Me | Me | H | F | H | H |
| IIA-10 | Ph | Q1 | Me | CF₃ | H | H | H | H |
| IIA-11 | 4-F-Ph | Q1 | Me | H | H | H | H | H |
| IIA-12 | 2,3-(MeO)₂-Ph | Q1 | Me | H | H | H | H | H |
| IIA-13 | 2,4-(MeO)₂-Ph | Q1 | Me | H | H | H | H | H |
| IIA-14 | 2-Cl-Ph | Q1 | Me | H | H | H | H | H |
| IIA-15 | 3,4-Cl₂-Ph | Q1 | Me | H | H | H | H | H |
| IIA-16 | Ph | Q2 | Et | H | CN | H | H | H |
| IIA-17 | Ph | Q2 | Et | H | CO₂H | H | H | H |
| IIA-18 | Ph | Q2 | Me | H | F | H | H | H |
| IIA-19 | Ph | Q2 | Me | H | H | F | H | H |
| IIA-20 | Ph | Q2 | Me | H | H | COMe | H | H |
| IIA-21 | Ph | Q2 | Me | H | H | COPh | H | H |
| IIA-22 | Et | Q1 | Me | H | H | H | H | H |
| IIA-23 | PhCH₂OCH₂— | Q1 | Me | H | H | H | H | H |
| IIA-24 | Ph | Q2 | Me | H | H | CONH₂ | H | H |
| IIA-25 | 3-F-Ph | Q1 | Me | H | CN | H | H | H |
| IIA-26 | 3-F-Ph | Q1 | Me | H | H | CN | H | H |
| IIA-27 | 3-F-Ph | Q1 | Me | H | F | H | H | H |
| IIA-28 | 3-F-Ph | Q1 | Me | H | H | F | H | H |
| IIA-29 | 3-F-Ph | Q1 | Me | H | Me | CN | H | H |
| IIA-30 | 3-F-Ph | Q1 | Me | H | F | CN | H | H |
| IIA-31 | 3-F-Ph | Q1 | Me | H | H | SMe | H | H |
| IIA-32 | Ph | Q1 | Me | H | F | CN | H | H |
| IIA-33 | Ph | Q1 | Me | H | F | H | H | H |
| IIA-34 | Ph | Q1 | Me | H | H | CN | H | H |
| IIA-35 | Ph | Q1 | Me | H | H | COMe | H | H |
| IIA-36 | Ph | Q1 | Me | H | CH=CH | H | H | H |
| IIA-37 | Ph | Q1 | Me | H | SMe | H | H | H |
| IIA-38 | Ph | Q1 | Me | H | Me | CN | H | H |
| IIA-39 | Ph | Q1 | Me | H | COMe | H | H | H |
| IIA-40 | Ph | Q2 | Et | H | H | H | H | H |
| IIA-41 | Ph | Q1 | Me | OMe | H | H | H | H |
| IIA-42 | Ph | Q1 | Me | H | H | F | H | H |
| IIA-43 | Ph | Q2 | Me | H | CO₂H | H | H | H |
| IIA-44 | Ph | Q1 | Me | H | H | Ph | H | H |
| IIA-45 | Ph | Q1 | Me | H | Me | H | Me | H |
| IIA-46 | Ph | Q1 | Me | H | H | SMe | H | H |
| IIA-47 | Ph | Q2 | Me | H | H | OMe | H | H |
| IIA-48 | Ph | Q2 | Me | H | OMe | H | H | H |
|  | Ph | Q1 | Me | OMe | H | H | CN | H |
| IIA-50 | Ph | Q2 | Me | H | CO₂Me | H | H | H |

TABLE 1-continued

Examples of Compounds of Formula IIA

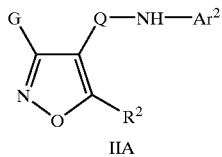

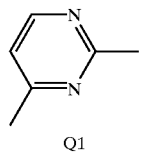 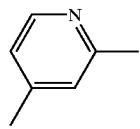 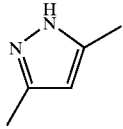

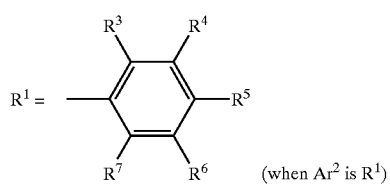

(when Ar² is R¹)

| No. | G | Q | $R^2$ | $R^3$ | $R^4$ | $R^5$ | $R^6$ | $R^7$ |
|---|---|---|---|---|---|---|---|---|
| IIA-51 | Ph | Q1 | Me | F | H | H | CN | H |
| IIA-52 | Ph | Q2 | Me | H | H | H | H | H |
| IIA-53 | Ph | Q2 | Me | H | H | $CO_2H$ | H | H |
| IIA-54 | Ph | Q1 | Me | Me | H | CN | H | H |
| IIA-55 | 2-F-Ph | Q1 | Me | H | H | H | H | H |
| IIA-56 | Ph | Q1 | Me | F | H | F | H | H |
| IIA-57 | Ph | Q1 | Me | Me | H | $CONH_2$ | H | H |
| IIA-58 | Ph | Q1 | Me | Me | Cl | H | H | H |
| IIA-59 | Ph | Q1 | Me | F | H | H | H | H |
| IIA-60 | 2,6-$F_2$-Ph | Q1 | Me | H | H | H | H | H |
| IIA-61 | Ph | Q1 | Me | Me | H | OMe | H | H |
| IIA-62 | Ph | Q1 | Me | OMe | H | H | H | H |
| IIA-63 | Ph | Q1 | Me | H | H | $SO_2Me$ | H | H |
| IIA-64 | Ph | Q2 | Me | H | H | $CO_2Me$ | H | H |
| IIA-65 | Ph | Q1 | Me | $NO_2$ | H | H | H | H |
| IIA-66 | 3-F-Ph | Q1 | Me | H | H | H | H | H |
| IIA-67 | Ph | Q2 | Me | H | CN | H | H | H |
| IIA-68 | Ph | Q2 | Me | H | H | CN | H | H |
| IIA-69 | Ph | Q1 | Me | CH:CH | H | H | H | H |
| IIA-70 | Ph | Q1 | Me | Me | F | H | H | H |
| IIA-71 | Ph | Q1 | Me | Cl | H | H | OMe | H |
| IIA-72 | Ph | Q1 | Me | H | Me | OMe | H | H |
| IIA-73 | Ph | Q1 | Me | OMe | H | H | OMe | H |
| IIA-74 | 2,5-$F_2$-Ph | Q1 | Me | H | H | H | H | H |
| IIA-75 | 2-Cl-6-F-Ph | Q1 | Me | H | H | H | H | H |
| IIA-76 | 2-Cl-Ph | Q1 | Me | H | H | H | H | H |
| IIA-77 | 3,4-$Cl_2$-Ph | Q1 | Me | H | H | H | H | H |
| IIA-78 | Ph | Q1 | Me | Me | H | F | H | H |
| IIA-79 | 2-Br-Ph | Q1 | Me | H | H | H | H | H |
| IIA-80 | 2,3-$F_2$-Ph | Q1 | Me | H | H | H | H | H |
| IIA-81 | Ph | Q1 | Me | SMe | H | H | H | H |
| IIA-82 | 3-$CF_3$-Ph | Q1 | Me | H | H | H | H | H |
| IIA-83 | 3,5-$F_2$-Ph | Q1 | Me | H | H | H | H | H |
| IIA-84 | 2,6-$Cl_2$-Ph | Q1 | Me | H | H | H | H | H |
| IIA-85 | 2,3-$(MeO)_2$-Ph | Q1 | Me | H | H | H | H | H |
| IIA-86 | Me | Q1 | Me | H | H | H | H | H |
| IIA-87 | cyclopropyl | Q1 | Me | H | H | H | H | H |
| IIA-88 | cyclohexyl | Q1 | Me | H | H | H | H | H |
| IIA-89 | 2,4-$(MeO)_2$-Ph | Q1 | Me | H | H | H | H | H |
| IIA-90 | t-butyl | Q1 | Me | H | H | H | H | H |
| IIA-91 | 2,6-$F_2$-Ph | Q1 | Me | H | H | COMe | H | H |
| IIA-92 | 2,6-$F_2$-Ph | Q1 | Me | H | CN | H | H | H |
| IIA-93 | 2,6-$F_2$-Ph | Q1 | Me | H | H | CN | H | H |
| IIA-94 | 2,6-$F_2$-Ph | Q1 | Me | H | F | H | H | H |
| IIA-95 | 2,6-$F_2$-Ph | Q1 | Me | H | H | F | H | H |
| IIA-96 | 2,6-$F_2$-Ph | Q1 | Me | H | CN | F | H | H |
| IIA-97 | 2,6-$F_2$-Ph | Q1 | Me | H | H | SMe | H | H |
| IIA-98 | Ph | Q2 | Me | H | H | $NMe_2$ | H | H |

TABLE 1-continued

Examples of Compounds of Formula IIA

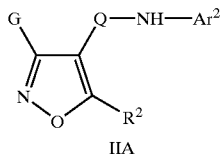

IIA

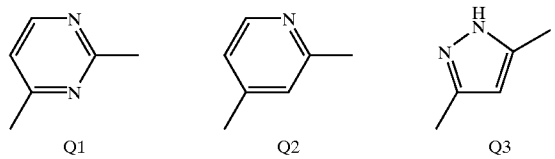

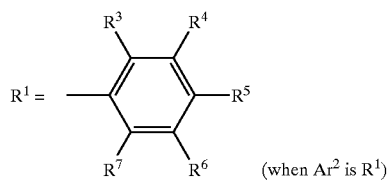

(when Ar² is R¹)

| No. | G | Q | R² | R³ | R⁴ | R⁵ | R⁶ | R⁷ |
|---|---|---|---|---|---|---|---|---|
| IIA-99 | Ph | Q2 | Me | H | NO₂ | H | H | H |
| IIA-100 | Ph | Q2 | Me | H | NHAc | H | H | H |
| IIA-101 | Ph | Q2 | Me | H | NH₂ | H | H | H |
| IIA-102 | Ph | Q1 | Me | H | Me | H | H | H |
| IIA-103 | Ph | Q1 | Me | H | H | Me | H | H |
| IIA-104 | 2-Me-Ph | Q1 | Me | H | H | H | H | H |
| IIA-105 | 2-Me-Ph | Q1 | Me | H | F | CN | H | H |
| IIA-106 | 2-Me-Ph | Q1 | Me | H | F | H | H | H |
| IIA-107 | 2-Me-Ph | Q1 | Me | H | H | CN | H | H |
| IIA-108 | 2-Me-Ph | Q1 | Me | H | Me | H | H | H |
| IIA-109 | 2-Me-Ph | Q1 | Me | H | CN | H | H | H |
| IIA-110 | 2-CF₃-Ph | Q1 | Me | H | F | CN | H | H |
| IIA-111 | 2-CF₃-Ph | Q1 | Me | H | CN | H | H | H |
| IIA-112 | 2-CF₃-Ph | Q1 | Me | H | H | H | H | H |
| IIA-113 | 3,4-(OCH₂O)-Ph | Q1 | Me | H | F | CN | H | H |
| IIA-114 | 3,4-(OCH₂O)-Ph | Q1 | Me | H | CN | H | H | H |
| IIA-115 | 3,4-(OCH₂O)-Ph | Q1 | Me | H | H | H | H | H |

IIA-116   Q1   Me

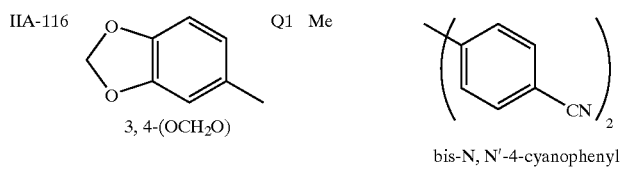

3, 4-(OCH₂O)        bis-N, N'-4-cyanophenyl

| IIA-117 | 3-OBn-Ph | Q1 | Me | H | F | CN | H | H |
|---|---|---|---|---|---|---|---|---|
| IIA-118 | 3-OBn-Ph | Q1 | Me | H | CN | H | H | H |
| IIA-119 | 3-OBn-Ph | Q1 | Me | H | H | H | H | H |
| IIA-120 | 3-NO₂-Ph | Q1 | Me | H | F | CN | H | H |
| IIA-121 | 3-NO₂-Ph | Q1 | Me | bis-N,N'-4-cyanophenyl | | | | |
| IIA-122 | 3-NO₂-Ph | Q1 | Me | H | CN | H | H | H |
| IIA-123 | 3-NO₂-Ph | Q1 | Me | H | H | H | H | H |
| IIA-124 | 3-CN-Ph | Q1 | Me | H | F | CN | H | H |
| IIA-125 | 3-CN-Ph | Q1 | Me | H | H | CN | H | H |

TABLE 1-continued
Examples of Compounds of Formula IIA
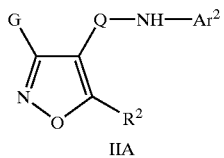
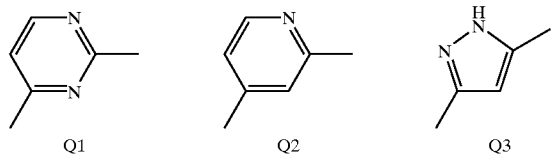
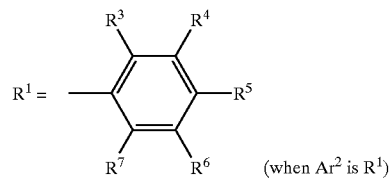
(when Ar² is R¹)
| No. | G | Q | R² | R³ | R⁴ | R⁵ | R⁶ | R⁷ |
|---|---|---|---|---|---|---|---|---|
| IIA-126 | 3-CN-Ph | Q1 | Me | H | CN | H | H | H |
| IIA-127 | 3-CN-Ph | Q1 | Me | H | H | H | H | H |
| IIA-128 | 3-NO$_2$-Ph | Q1 | Me | H | H | CO$_2$Et | H | H |
| IIA-129 | 3-CN-Ph | Q1 | Me | H | CO$_2$Me | H | H | H |
| IIA-130 | Ph | Q1 | Me | H | CO$_2$Et | H | H | H |
| IIA-131 | Ph | Q1 | Me | N | H | NO$_2$ | H | H |
| IIA-132 | Ph | Q2 | Me | 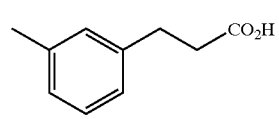 | | | | |
| IIA-133 | Ph | Q2 | Me | 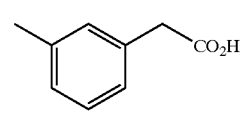 | | | | |
| IIA-134 | Ph | Q2 | Me | H | CH$_2$OH | H | H | H |
| IIA-135 | Ph | Q2 | Me | 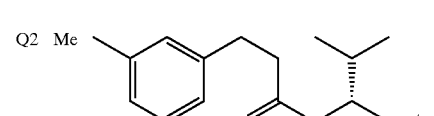 | | | | |
| IIA-136 | Ph | Q3 | Me | H | CN | H | H | H |
| IIA-137 | Ph | Q3 | Me | H | H | CN | H | H |
| IIA-138 | Ph | Q3 | Me | H | COMe | H | H | H |

For compounds of Formula IIA where R¹ is phenyl, preferred phenyl substituents are selected from hydrogen and one or more halo, aliphatic, substituted aliphatic (preferably haloalkyl), alkoxy, CN, $CO_2H$, $CO_2$(alkyl), S(alkyl), $CONH_2$, CO(alkyl), $SO_2$(alkyl), CO(phenyl), or $NO_2$. Preferred G groups are phenyl rings optionally substituted with one or more groups independently selected from alkyl, alkoxy or halogen.

Examples of compounds of Formula IIA where R¹ is other than phenyl are shown below in Table 2.

TABLE 2

Examples of Compounds of Formula IIA (R¹ is other than phenyl)

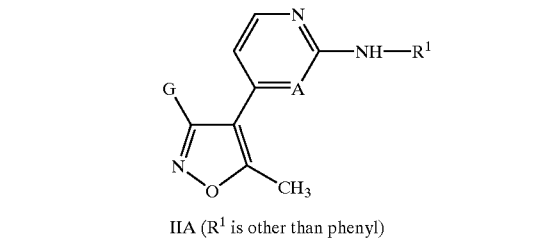

IIA (R¹ is other than phenyl)

| No. | G | A | R¹ |
|---|---|---|---|
| IIAA-1 | Ph | CH | 3-pyridyl |
| IIAA-2 | Ph | CH | 6-methoxy-3-pyridyl |
| IIAA-3 | Ph | N | 4-methyl-1-naphthyl |
| IIAA-4 | Ph | N | 2-naphthyl |
| IIAA-5 | Ph | N | 3-pyridyl |
| IIAA-6 | Ph | N | 4-isoquinolinyl |
| IIAA-7 | Ph | N | 8-quinolinyl |

TABLE 2-continued

Examples of Compounds of Formula IIA (R¹ is other than phenyl)

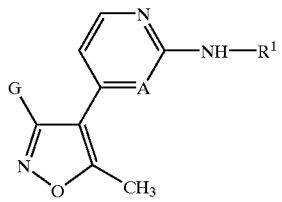

IIA (R¹ is other than phenyl)

| No. | G | A | R¹ |
|---|---|---|---|
| IIAA-8 | Ph | N | 2-methyl-6-quinolinyl |
| IIAA-9 | 3-F-Ph | N | 6-methoxy-2-naphthyl |
| IIAA-10 | Ph | N | 6-methoxy-2-naphthyl |
| IIAA-11 | Ph | N | 1-oxo-indan-5-yl |
| IIAA-12 | Ph | N | 4-methyl-2-pyridyl |
| IIAA-13 | Ph | N | 8-naphthyl |
| IIAA-14 | 2,6-$F_2$-Ph | N | 6-methoxy-2-naphthyl |
| IIAA-15 | Ph | N | 2-methyl-1-naphthyl |
| IIAA-16 | Ph | N | 6-methoxycarbonyl-2-naphthyl |

TABLE 2-continued
Examples of Compounds of Formula IIA (R¹ is other than phenyl)
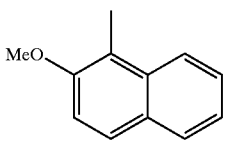
IIA (R¹ is other than phenyl)
| No. | G | A | R¹ |
|---|---|---|---|
| IIAA-17 | Ph | N | 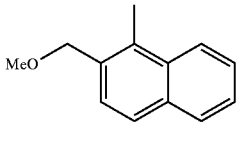 |
| IIAA-18 | Ph | N | 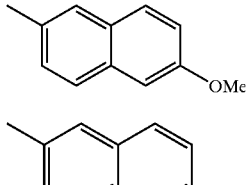 |
| IIAA-19 | 2-Me-Ph | N | 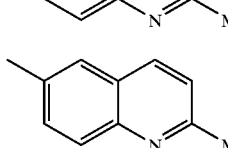 |
| IIAA-20 | 2-Me-Ph | N | 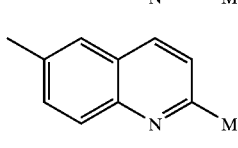 |
| IIAA-21 | 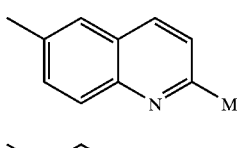 | N | 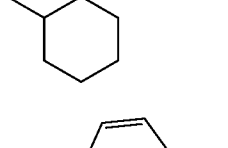 |
| IIAA-22 | 3-NO₂-Ph | N | 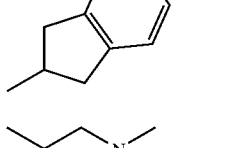 |
| IIAA-23 | 3-CN-Ph | N | 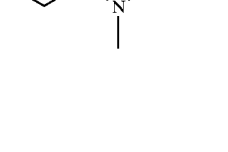 |
| IIAA-24 | Ph | N |  |
| IIAA-25 | Ph | N | 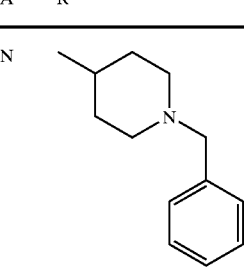 |
| IIAA-26 | Ph | N | 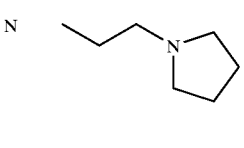 |
| IIAA-27 | Ph | N | 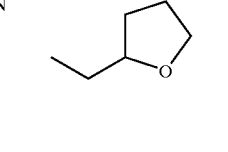 |
| IIAA-28 | Ph | N | 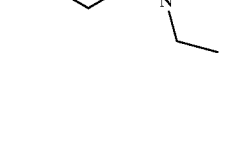 |
| IIAA-29 | Ph | N | 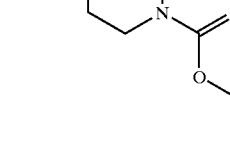 |
| IIAA-30 | Ph | N | 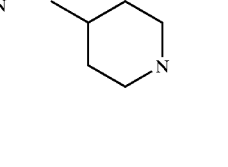 |
| IIAA-31 | Ph | N |  |
| IIAA-32 | Ph | N |  |

TABLE 2-continued

Examples of Compounds of Formula IIA ($R^1$ is other than phenyl)

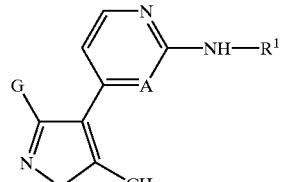

IIA ($R^1$ is other than phenyl)

| No. | G | A | $R^1$ |
|---|---|---|---|
| IIAA-33 | Ph | N | isobutyl-OH |
| IIAA-34 | Ph | N | isobutyl-OMe |
| IIAA-35 | Ph | N | ethyl isovalerate |
| IIAA-36 | Ph | N | trans-4-hydroxycyclohexyl |
| IIAA-37 | Ph | N | isovaleric acid |
| IIAA-38 | Ph | N | 4-methylcyclohexanone |
| IIAA-39 | Ph | CH | propyl-morpholine |
| IIAA-40 | Ph | CH | ethyl-2-pyridyl |

Preferred IIA compounds are those where $Ar^1$ is an unsubstituted phenyl or a phenyl substituted with one or more halo, alkyl or alkoxy. More preferred IIA compounds are those where $Ar^1$ is as just described, and $Ar^2$ is a naphthyl or phenyl optionally substituted with one or more halo, alkyl, alkoxy, haloalkyl, carboxyl, alkoxycarbonyl, cyano, or $CONH_2$, or an indanone (as in compound IIAA-11). Also preferred are IIA compounds where $R^1$ is an optionally substituted alkyl or optionally substituted cycloalkyl, more preferably alkoxyalkyl, alkoxycarbonylalkyl, hydroxyalkyl, pyridinylalkyl, alkoxycycloalkyl, alkoxycarbonylcycloalkyl, or hydroxycyloalkyl. Examples of these preferred compounds include IIAA-24, IIAA-33 through IIAA-36, IIAA-38 and IIAA-40.

One embodiment of this invention relates to compounds of formula IA where Q is a pyrimidine ring and $R^1$ is T—$Ar^2$ where T is selected from CO, $CO_2$, CONH, $S(O)_2$, $S(O)_2NH$, $COCH_2$ and $CH_2$. When $R^1$ is T—$Ar^2$, preferred compounds are those where T is C(=O), represented by formula IIIA. Table 3 below shows representative examples of IIIA compounds.

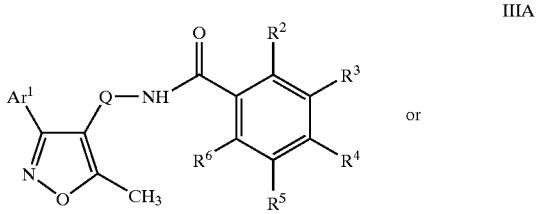

IIIA or

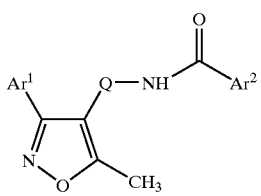

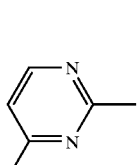

Q1

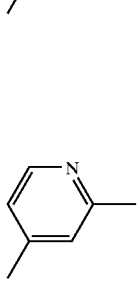

Q2

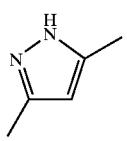

Q3

TABLE 3

Examples of IIIA Compounds

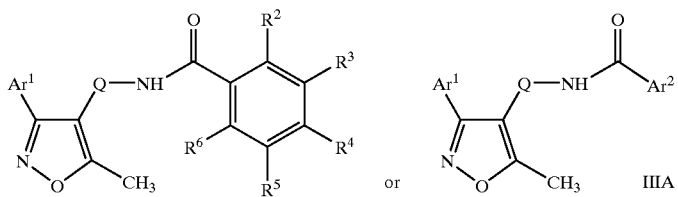

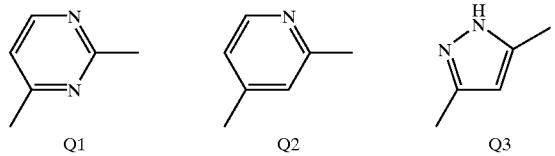

| No. | Ar¹ | Q | R² | R³ | R⁴ | R⁵ | R⁶ |
|---|---|---|---|---|---|---|---|
| IIIA-1 | phenyl | Q1 | H | H | H | H | H |
| IIIA-2 | phenyl | Q1 | Br | H | H | H | H |
| IIIA-3 | phenyl | Q1 | F | H | H | H | H |
| IIIA-4 | phenyl | Q1 | Cl | H | H | H | H |
| IIIA-5 | phenyl | Q1 | CH₃ | H | H | H | H |
| IIIA-6 | phenyl | Q1 | H | CH₃ | H | H | H |
| IIIA-7 | phenyl | Q1 | H | H | OCH₃ | H | H |
| IIIA-8 | phenyl | Q1 | H | OCH₃ | OCH₃ | H | H |
| IIIA-9 | phenyl | Q1 | OCH₃ | H | OCH₃ | H | H |
| IIIA-10 | phenyl | Q1 | OCH₃ | H | H | H | OCH₃ |
| IIIA-11 | phenyl | Q1 | H | H | CN | H | H |
| IIIA-12 | 5-fluorophenyl | Q1 | H | H | OCH₃ | H | H |
| IIIA-13 | phenyl | Q1 | H | OCH₃ | OCH₃ | OCH₃ | H |
| IIIA-14 | phenyl | Q1 | H | H | F | H | H |
| IIIA-15 | phenyl | Q1 | Ar² is 2-thienyl | | | | |
| IIIA-16 | phenyl | Q1 | Ar² is 1-oxo-indan-5-yl | | | | |
| IIIA-17 | phenyl | Q1 | Ar² is 4-pyridyl | | | | |
| IIIA-18 | 2-CH₃-phenyl | Q1 | H | OCH₃ | OCH₃ | OCH₃ | H |
| IIIA-19 | 2-CH₃-phenyl | Q1 | H | OCH₃ | H | H | H |
| IIIA-20 | 2-CH₃-phenyl | Q1 | H | H | OCH₃ | H | H |
| IIIA-21 | 2-CH₃-phenyl | Q1 | H | OCH₃ | H | OCH₃ | H |
| IIIA-22 | 2-CF₃-phenyl | Q1 | H | OCH₃ | OCH₃ | OCH₃ | H |
| IIIA-23 | 2-CF₃-phenyl | Q1 | H | OCH₃ | H | H | H |
| IIIA-24 | 2-CF₃-phenyl | Q1 | H | H | OCH₃ | H | H |
| IIIA-25 | 2-CF₃-phenyl | Q1 | H | OCH₃ | H | OCH₃ | H |
| IIIA-26 | benzo[3,5]dioxole | Q1 | H | OCH₃ | OCH₃ | OCH₃ | H |
| IIIA-27 | benzo[3,5]dioxole | Q1 | H | OCH₃ | H | H | H |
| IIIA-28 | benzo[3,5]dioxole | Q1 | H | H | OCH₃ | H | H |
| IIIA-29 | benzo[3,5]dioxole | Q1 | H | OCH₃ | H | OCH₃ | H |
| IIIA-30 | 3-benzyloxy-phenyl | Q1 | H | OCH₃ | OCH₃ | OCH₃ | H |
| IIIA-31 | 3-benzyloxy-phenyl | Q1 | H | OCH₃ | H | H | H |
| IIIA-32 | 3-benzyloxy-phenyl | Q1 | H | H | OCH₃ | H | H |
| IIIA-33 | 3-benzyloxy-phenyl | Q1 | H | OCH₃ | H | OCH₃ | H |
| IIIA-34 | 3-nitrophenyl | Q1 | H | OCH₃ | OCH₃ | OCH₃ | H |
| IIIA-35 | 3-nitrophenyl | Q1 | H | OCH₃ | H | H | H |
| IIIA-36 | 3-nitrophenyl | Q1 | H | H | OCH₃ | H | H |
| IIIA-37 | 3-nitrophenyl | Q1 | H | OCH₃ | H | OCH₃ | H |
| IIIA-38 | 3-cyanophenyl | Q1 | H | OCH₃ | OCH₃ | OCH₃ | H |
| IIIA-39 | 3-cyanophenyl | Q1 | H | OCH₃ | H | H | H |
| IIIA-40 | 3-cyanophenyl | Q1 | H | H | OCH₃ | H | H |
| IIIA-41 | 3-cyanophenyl | Q1 | H | OCH₃ | H | OCH₃ | H |
| IIIA-42 | phenyl | Q1 | H | OCH₃ | H | OCH₃ | H |
| IIIA-43 | phenyl | Q1 | H | CN | H | H | H |
| IIIA-44 | phenyl | Q1 | H | H | CO₂Me | H | H |
| IIIA-45 | 3-fluorophenyl | Q1 | H | Cl | H | H | H |
| IIIA-46 | 3-fluorophenyl | Q1 | H | OCH₃ | H | H | H |
| IIIA-47 | 3-fluorophenyl | Q1 | H | OCH₃ | H | OCH₃ | H |
| IIIA-48 | 3-fluorophenyl | Q1 | H | Me | H | H | H |
| IIIA-49 | 3-fluorophenyl | Q1 | H | H | F | H | H |
| IIIA-50 | 3-fluorophenyl | Q1 | H | H | Me | H | H |
| IIIA-51 | 3-fluorophenyl | Q1 | H | CN | H | H | H |
| IIIA-52 | 3-fluorophenyl | Q1 | H | OCH₃ | OCH₃ | OCH₃ | H |
| IIIA-53 | 3-fluorophenyl | Q1 | Ar² is 2-naphthyl | | | | |
| IIIA-54 | 2-fluorophenyl | Q1 | H | Cl | H | H | H |

TABLE 3-continued

Examples of IIIA Compounds

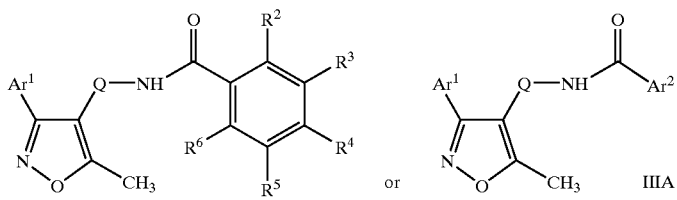

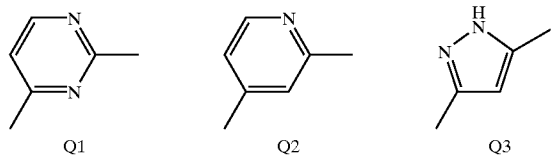

| No. | Ar¹ | Q | R² | R³ | R⁴ | R⁵ | R⁶ |
|---|---|---|---|---|---|---|---|
| IIIA-55 | 2-fluorophenyl | Q1 | H | OCH₃ | H | H | H |
| IIIA-56 | 2-fluorophenyl | Q1 | H | OCH₃ | H | OCH₃ | H |
| IIIA-57 | 2-fluorophenyl | Q1 | H | Me | H | H | H |
| IIIA-58 | 2-fluorophenyl | Q1 | H | H | OCH₃ | H | H |
| IIIA-59 | 2-fluorophenyl | Q1 | H | H | F | H | H |
| IIIA-60 | 2-fluorophenyl | Q1 | H | H | Me | H | H |
| IIIA-61 | 2-fluorophenyl | Q1 | H | CN | H | H | H |
| IIIA-62 | 2-fluorophenyl | Q1 | H | OCH₃ | OCH₃ | OCH₃ | H |
| IIIA-63 | 2-fluorophenyl | Q1 | Ar² is 2-naphthyl | | | | |
| IIIA-64 | 2,6-F₂-phenyl | Q1 | H | Cl | H | H | H |
| IIIA-65 | 2,6-F₂-phenyl | Q1 | H | OCH₃ | H | H | H |
| IIIA-66 | 2,6-F₂-phenyl | Q1 | H | OCH₃ | H | OCH₃ | H |
| IIIA-67 | 2,6-F₂-phenyl | Q1 | H | Me | H | H | H |
| IIIA-68 | 2,6-F₂-phenyl | Q1 | H | H | OCH₃ | H | H |
| IIIA-69 | 2,6-F₂-phenyl | Q1 | H | H | F | H | H |
| IIIA-70 | 2,6-F₂-phenyl | Q1 | H | H | Me | H | H |
| IIIA-71 | 2,6-F₂-phenyl | Q1 | H | CN | H | H | H |
| IIIA-72 | 2,6-F₂-phenyl | Q1 | H | OCH₃ | OCH₃ | OCH₃ | H |
| IIIA-73 | 2,6-F₂-phenyl | Q1 | Ar² is 2-naphthyl | | | | |
| IIIA-74 | phenyl | Q1 | H | NO₂ | H | H | H |
| IIIA-75 | phenyl | Q1 | H | NHAc | H | H | H |
| IIIA-76 | phenyl | Q1 | H | COMe | H | H | H |
| IIIA-77 | phenyl | Q2 | H | COMe | H | H | H |
| IIIA-78 | phenyl | Q2 | H | CN | H | H | H |
| IIIA-79 | phenyl | Q3 | H | H | H | H | H |
| IIIA-80 | phenyl | Q3 | H | OCH₃ | H | H | H |
| IIIA-81 | phenyl | Q3 | H | H | OCH₃ | H | H |
| IIIA-82 | phenyl | Q3 | H | CN | H | H | H |
| IIIA-83 | phenyl | Q3 | H | OCH₃ | H | OCH₃ | H |
| IIIA-84 | phenyl | Q3 | H | H | F | H | H |
| IIIA-85 | phenyl | Q3 | H | COMe | H | H | H |
| IIIA-86 | phenyl | Q3 | H | H | COMe | H | H |
| IIIA-87 | phenyl | Q3 | OCH₃ | H | H | H | H |
| IIIA-88 | phenyl | Q3 | | | 2-thienyl | | |
| IIIA-89 | phenyl | Q3 | | | 2-furanyl | | |
| IIIA-90 | 3-OMe-phenyl | Q3 | H | OCH₃ | H | H | H |
| IIIA-91 | Cyclohexyl | Q3 | H | OCH₃ | H | H | H |
| IIIA-92 | 4-Cl-phenyl | Q3 | H | OCH₃ | H | H | H |
| IIIA-93 | 3-Cl-phenyl | Q3 | H | OCH₃ | H | H | H |
| IIIA-94 | 4-F-phenyl | Q3 | H | OCH₃ | H | H | H |
| IIIA-95 | 3-F-phenyl | Q3 | H | OCH₃ | H | H | H |
| IIIA-96 | 4-pyridyl | Q3 | H | OCH₃ | H | H | H |
| IIIA-97 | 3-pyridyl | Q3 | H | OCH₃ | H | H | H |

Preferred IIIA compounds are those compounds where Ar¹ is an unsubstituted phenyl or a phenyl substituted with one or more substituents independently selected from halogen. More preferred IIIA compounds are those where Ar¹ is just described, and Ar² is a thienyl, an unsubstituted phenyl or a phenyl substituted with one or more substituents independently selected from halogen, alkyl, alkoxy, $CO_2H$ or $CO_2R$.

Examples of other compounds where $R^1$ is T-Ar¹ are shown below where A is N or CH, and T is one of the following: $CH_2$ (exemplified by IVA-1), $S(O)_2$ (VA-1), CONH (VIA-1), $COCH_2$ (VIIA-1), $CO_2$, (VIIIA-1), and $S(O)_2NH$ (IXA-1). In other examples of these embodiments the phenyl rings may be optionally substituted as described above.

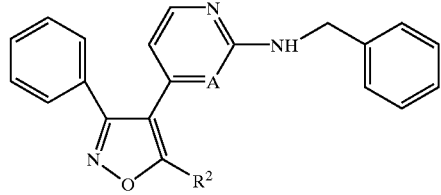

IVA-1

(R² = CH₃)

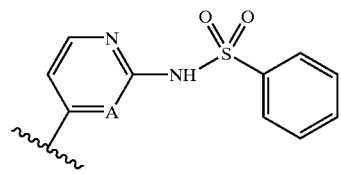

VA-1

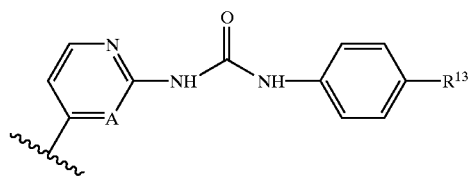

VIA-1 (R¹³ = H)
VIA-2 (R¹³ = OMe)
VIA-3 (thiourea of 1)

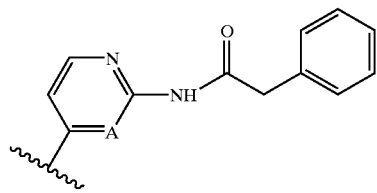

VIIA-1

VIIIA-1

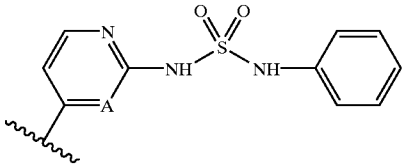

IXA-1

Another embodiment of this invention relates to compounds of formula IA where $R^1$ is T—R, R is a $C_3$–$C_6$ cycloalkyl ring or a $C_1$–$C_6$ straight chain or branched alkyl or alkenyl group optionally substituted by halogen and T is as described above. When $R^1$ is T—R, preferred compounds are those where T is C(=O) as represented by formula XA. Table 4 below shows representative examples of XA compounds.

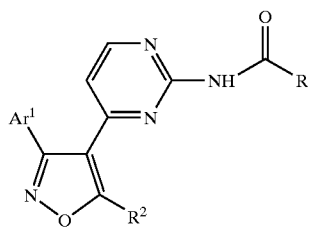

XA

TABLE 4

Examples of XA Compounds ($R^2$ is CH₃)

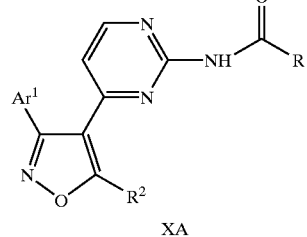

XA

| No. | Ar¹ | R |
|---|---|---|
| XA-1 | phenyl | CH₃ |
| XA-2 | 4-F-phenyl | CH₃ |
| XA-3 | phenyl | Cyclopentyl |
| XA-4 | phenyl | isobutyl |
| XA-5 | phenyl | propyl |

Preferred $R^2$ groups of formula I include —CH₂OR, —CH₂OH, —CH₂ (heterocyclyl), —CH₂ (substituted heterocyclyl), —CH₂N(R)₂₁ and an R group such as methyl. Representative examples of compounds wherein $R^2$ is other than methyl (formula IXA) are shown in Table 5 below.

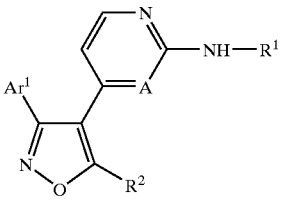

IXA ($R^2$ is other than CH₃)

TABLE 5

Examples of Compound IXA

![IXA structure]

IXA  (R² is other than CH₃)

| No. | Ar¹ | A | R¹ | R² |
|---|---|---|---|---|
| XIA-1 | phenyl | CH | phenyl | CH$_2$(morpholin-4-yl) |
| XIA-2 | phenyl | CH | phenyl | CH$_2$N(CH$_3$)$_2$ |
| XIA-3 | phenyl | CH | phenyl | CH$_2$NEt$_2$ |
| XIA-4 | phenyl | CH | phenyl | CH$_2$N(CH$_3$)CH$_2$Ph |
| XIA-5 | phenyl | CH | phenyl | CH$_2$(1-t-butoxycarbonylpiperazin-4-yl) |
| XIA-6 | phenyl | CH | benzyl | CH$_2$(morpholin-4-yl) |
| XIA-7 | phenyl | CH | cyclohexyl | CH$_2$(morpholin-4-yl) |
| XIA-8 | phenyl | CH | 4-[1,2-(OMe)$_2$-phenyl] | CH$_2$(morpholin-4-yl) |
| XIA-9 | phenyl | CH | 4-cyclohexanol | CH$_2$(morpholin-4-yl) |
| XIA-10 | phenyl | CH | phenyl | CH$_2$N(CH$_3$)CH$_2$CH$_2$N(CH$_3$)$_2$ |
| XIA-11 | phenyl | CH | phenyl | CH$_2$N(CH$_3$)CH$_2$CO$_2$CH$_3$ |
| XIA-12 | phenyl | CH | phenyl | CH$_2$(piperazin-1-yl) |
| XIA-13 | phenyl | N | 2-thienoyl | CH$_2$Br |
| XIA-14 | phenyl | N | 2-thienoyl | CH$_2$(morpholin-4-yl) |
| XIA-15 | 4-F-phenyl | CH | cyclohexyl | CH$_2$O(tetrahydrofuran-3-yl) |
| XIA-16 | 4-F-phenyl | CH | 3-cyanophenyl | CH$_2$O(tetrahydrofuran-3-yl) |
| XIA-17 | 4-F-phenyl | CH | (2-pyridinyl)ethyl | CH$_2$O(tetrahydrofuran-3-yl) |
| XIA-18 | 4-F-phenyl | CH | 1-benzyl-piperidin-4-yl | CH$_2$O(tetrahydrofuran-3-yl) |
| XIA-19 | 4-F-phenyl | CH | 4-cyclohexanol | CH$_2$OCH$_2$CH$_2$OCH$_3$ |
| XIA-20 | 4-F-phenyl | CH | cyclohexyl | CH$_2$OCH$_2$CH$_2$OCH$_3$ |
| XIA-21 | 4-F-phenyl | CH | 2-(2-pyridinyl)ethyl | CH$_2$OCH$_2$CH$_2$OCH$_3$ |
| XIA-22 | 4-F-phenyl | CH | 1-benzyl-piperidin-4-yl | CH$_2$OCH$_2$CH$_2$OCH$_3$ |
| XIA-23 | 4-F-phenyl | CH | 4-cyclohexanol | CH$_2$(morpholin-4-yl) |
| XIA-24 | 4-F-phenyl | CH | cyclohexyl | CH$_2$(morpholin-4-yl) |
| XIA-25 | 4-F-phenyl | CH | 3-cyanophenyl | CH$_2$(morpholin-4-yl) |
| XIA-26 | 4-F-phenyl | CH | 2-(2-pyridinyl)ethyl | CH$_2$(morpholin-4-yl) |
| XIA-27 | 4-F-phenyl | CH | 1-benzyl-piperidin-4-yl | CH$_2$(morpholin-4-yl) |
| XIA-28 | 4-F-phenyl | CH | 4-cyclohexanol | CH$_2$OCH$_3$ |
| XIA-29 | 4-F-phenyl | CH | cyclohexyl | CH$_2$OCH$_3$ |
| XIA-30 | 4-F-phenyl | CH | 3-cyanophenyl | CH$_2$OCH$_3$ |
| XIA-31 | 4-F-phenyl | CH | 2-(2-pyridinyl)ethyl | CH$_2$OCH$_3$ |
| XIA-32 | 4-F-phenyl | CH | 1-benzyl-piperidin-4-yl | CH$_2$OCH$_3$ |
| XIA-33 | 4-F-phenyl | CH | 4-cyclohexanol | CH$_2$OCH$_3$ |
| XIA-34 | 4-F-phenyl | CH | cyclohexyl | CH$_2$OCH$_3$ |
| XIA-35 | 4-F-phenyl | CH | 3-cyanophenyl | CH$_2$OCH$_3$ |
| XIA-36 | 4-F-phenyl | CH | 2-(2-pyridinyl)ethyl | CH$_2$OCH$_3$ |
| XIA-37 | 4-F-phenyl | CH | 4-cyclohexanol | CH$_2$O(tetrahydrofuran-3-yl) |
| XIA-38 | 4-F-phenyl | CH | cyclohexyl | CH$_2$O(tetrahydrofuran-3-yl) |
| XIA-39 | phenyl | N | 2-thienoyl | CH$_2$(piperidin-1-yl) |
| XIA-40 | phenyl | N | 2-thienoyl | CH$_2$(piperazin-1-yl) |
| XIA-41 | 4-F-phenyl | CH | 4-methoxybenzyl | CH$_2$OCH$_3$ |
| XIA-42 | 4-F-phenyl | N | 4-cyclohexanol | CH$_2$(morpholin-4-yl) |
| XIA-43 | 4-F-phenyl | N | cyclohexyl | CH$_2$OCH$_2$CH$_3$ |
| XIA-44 | 4-F-phenyl | N | cyclohexyl | CH$_2$OCH$_2$(phenyl) |
| XIA-45 | 4-F-phenyl | N | cyclohexyl | CH$_2$OH |
| XIA-46 | 4-F-phenyl | N | CH$_2$CH$_2$(pyridin-2-yl) | CH$_2$OH |
| XIA-47 | 4-F-phenyl | N | cyclohexyl | CH$_2$OCH$_3$ |
| XIA-48 | 4-F-phenyl | N | cyclohexyl | CH$_2$OCH$_2$CH$_3$ |
| XIA-49 | 4-F-phenyl | N | cyclohexyl | CH$_2$OCH$_2$CH$_2$OCH$_3$ |
| XIA-50 | 4-F-phenyl | N | cyclohexyl | CH$_2$O(tetrahydrofuran-3-yl) |
| XIA-51 | 4-F-phenyl | N | cyclohexyl | 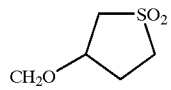 |

TABLE 5-continued

Examples of Compound IXA

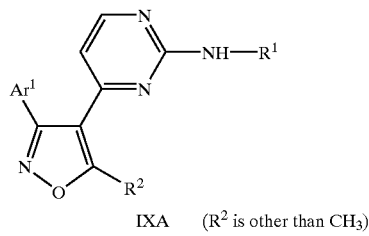

IXA ($R^2$ is other than $CH_3$)

| No. | $Ar^1$ | A | $R^1$ | $R^2$ |
|---|---|---|---|---|
| XIA-52 | 4-F-phenyl | N | cyclohexyl | $CH_2OCH_2$(phenyl) |
| XIA-53 | 4-F-phenyl | N | $CH_2CH_2$(pyridin-2-yl) | $CH_2OCH_2$(phenyl) |

The XYZ-containing ring of formula I may be an isoxazole ring as shown above or it may an isomeric isoxazole or "reverse" isoxazole (IB). In this embodiment Q is preferably a pyrimidine or pyridine ring where A is N or CH, or Q is a pyrazole ring, and $R^2$ is aliphatic or substituted aliphatic.

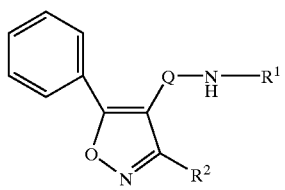

IB

Examples of IB compounds are shown in Table 6 below.

TABLE 6

IB-1

IB-2

IB-3

TABLE 6-continued

IB-4

IB-5

IB-6

IB-7

TABLE 6-continued
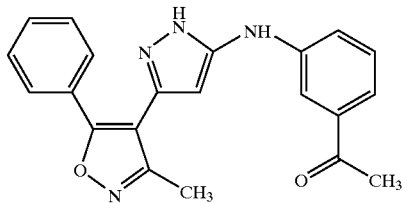
IB-8
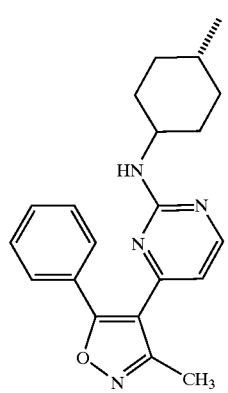
IB-9
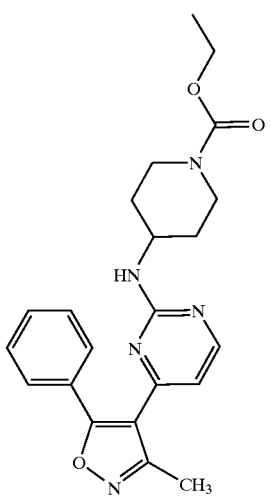
IB-10
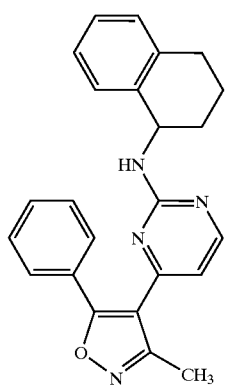
TABLE 6-continued
IB-11
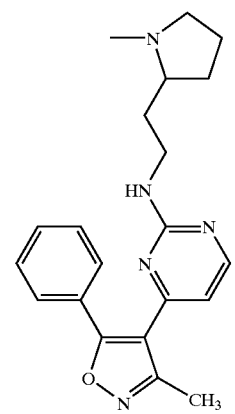
IB-12
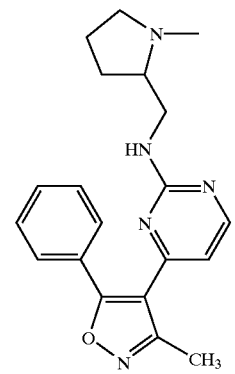
IB-13
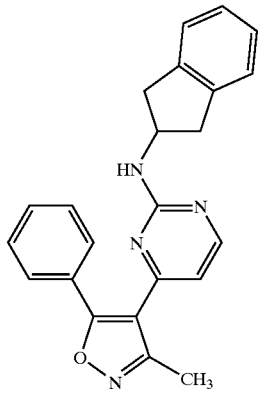
IB-14

TABLE 6-continued
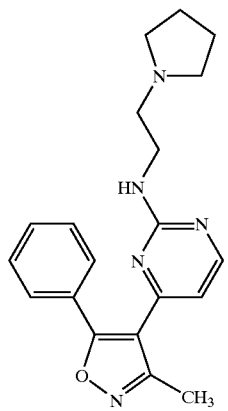
IB-15
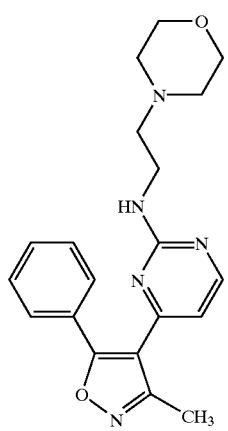
IB-16
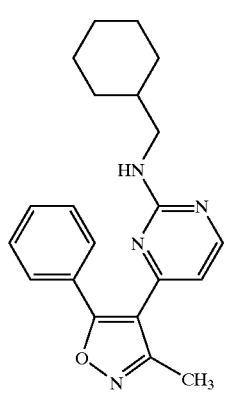
IB-17
TABLE 6-continued
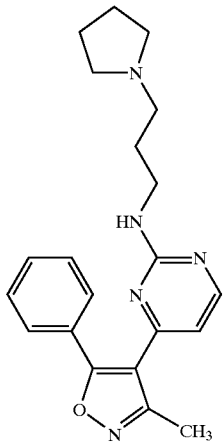
IB-18
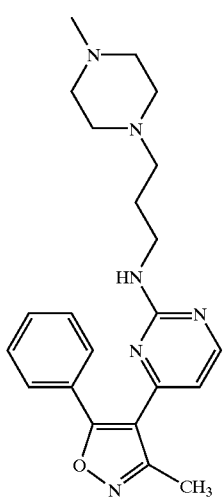
IB-19
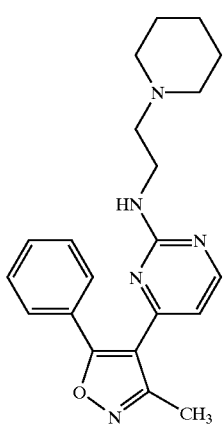
IB-20

TABLE 6-continued
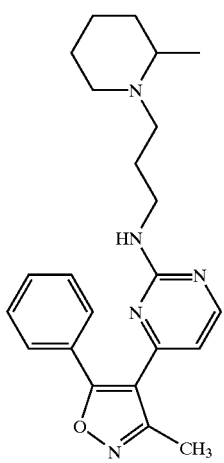
IB-21
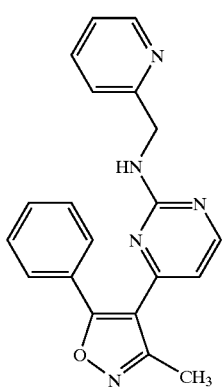
IB-22
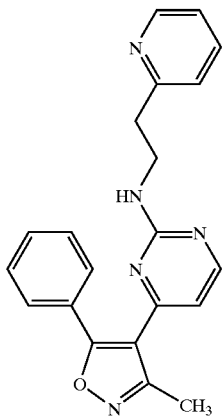
IB-23
TABLE 6-continued
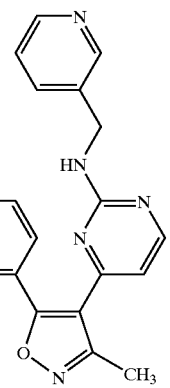
IB-24
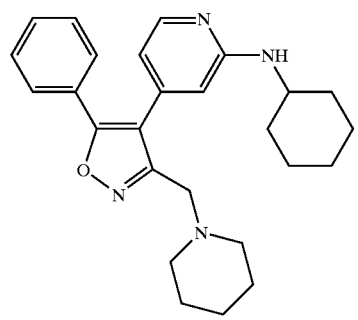
In another embodiment of this invention, the XYZ-containing ring is a pyrazole ring of formula IC:
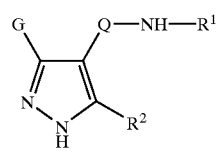
IC
For compounds of formula IC, G is preferably an optionally substituted aryl. Specific examples of IC compounds are shown in Table 7 below.
Q1
Q2
Q3

TABLE 7

Examples of IC Compounds

| No. | G | Q | $R^1$ | $R^2$ |
|---|---|---|---|---|
| IC-1 | 4-F-phenyl | Q2 | Phenyl | H |
| IC-2 | 4-F-phenyl | Q2 | Cyclohexyl | H |
| IC-3 | 4-F-phenyl | Q2 | Isoquinolin-4-yl | H |
| IC-4 | 4-F-phenyl | Q2 | 6-MeO-naphthalen-2-yl | H |
| IC-5 | 4-F-phenyl | Q2 | 4-cyclohexanol | H |
| IC-6 | 4-F-phenyl | Q1 | Phenyl | H |
| IC-7 | 4-F-phenyl | Q1 | Cyclohexyl | H |
| IC-8 | 4-F-phenyl | Q1 | 4-cyclohexanol | H |
| IC-9 | 4-F-phenyl | Q2 | Cyclohexyl | $CH_3$ |
| IC-10 | 4-F-phenyl | Q2 | Cyclohexyl | 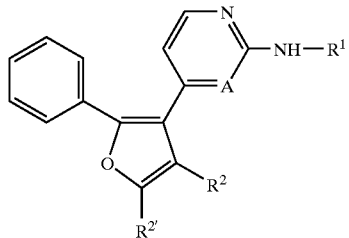 |
| IC-11 | Phenyl | Q2 | Cyclohexyl | 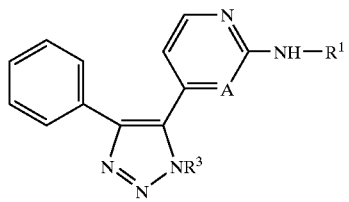 |

Other embodiments of this invention relate to compounds where the XYZ-containing ring is a furan (ID) or a triazole (IE). These embodiments are exemplified below where $R^1$ is phenyl, $R^{2'}$ is hydrogen, and A is N or CH.

ID-1 ($R^2$ = H)
ID-2 ($R^2$ = $CH_3$)

IE-1 ($R^3$ = H)
IE-1 ($R^3$ = $CH_3$)

For compounds of formula IB-IE, the phenyl rings of $Ar^1$ and $Ar^2$ may be optionally substituted as shown above for the isoxazoles of formula IA.

The compounds of this invention may be prepared in general by methods known to those skilled in the art for analogous compounds, as illustrated by the general schemes below and by the preparative examples that follow.

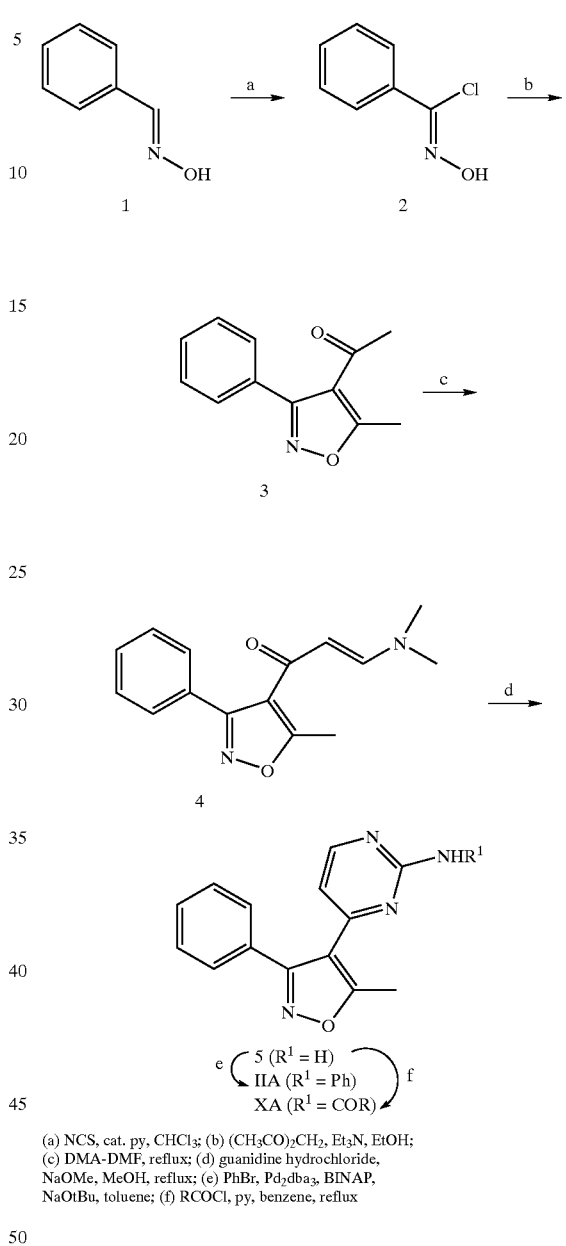

Scheme I (a) NCS, cat. py, $CHCl_3$; (b) $(CH_3CO)_2CH_2$, $Et_3N$, EtOH;
(c) DMA-DMF, reflux; (d) guanidine hydrochloride, NaOMe, MeOH, reflux; (e) PhBr, $Pd_2dba_3$, BINAP, NaOtBu, toluene; (f) RCOCl, py, benzene, reflux Scheme I above shows a route for making isoxazoles where Q is a pyrimidine ring. The starting benzaldehyde oxime 1 may be converted to the α-chlorobenzaldehyde oxime 2 using N-chlorosuccinimide and a catalytic amount of pyridine. Condensation of 2 with 2,4-pentanedione provides the isoxazole 3 which may be treated with dimethylformamide dimethylacetal to obtain the enamine 4. After an aqueous work-up and without purification, 4 may be cyclized with guanidine hydrochloride to the aminopyrimidine 5. Compounds of formula IIA may be obtained from 5 according to step (e) using the appropriate arylbromide in the presence of tris(dibenylideneacetone) dipalladium. Alternatively, 5 may be treated with the appropriate acid chloride in a pyridine/benzene solvent according to step (f)

to give compounds of formula IVA. If the acid chloride is a Ar²COCl, compounds of formula IIIA may be obtained in a similar manner.

Scheme II

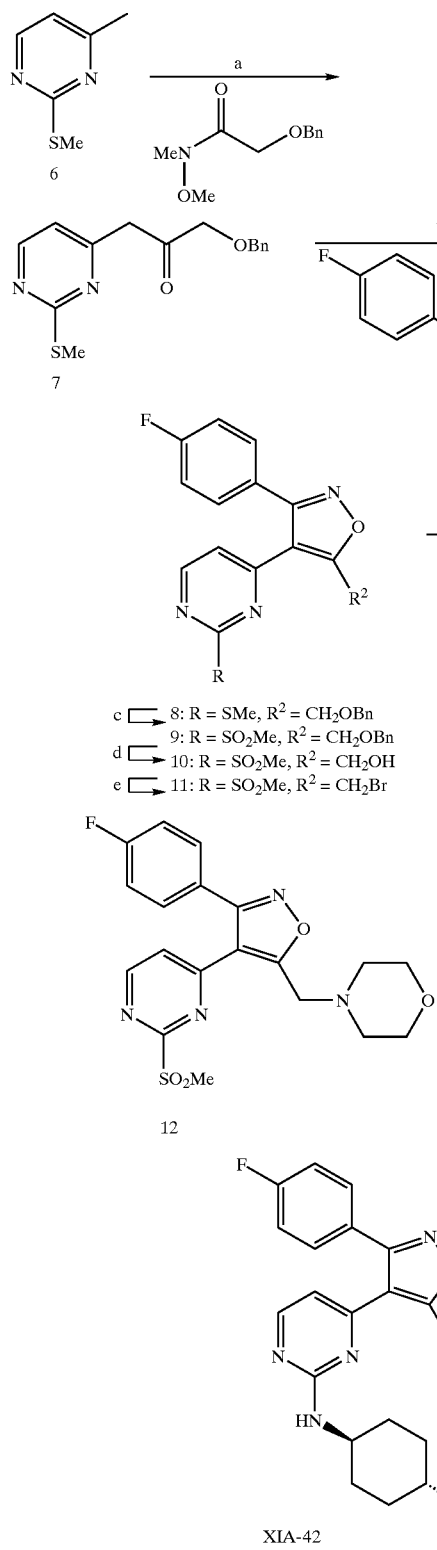

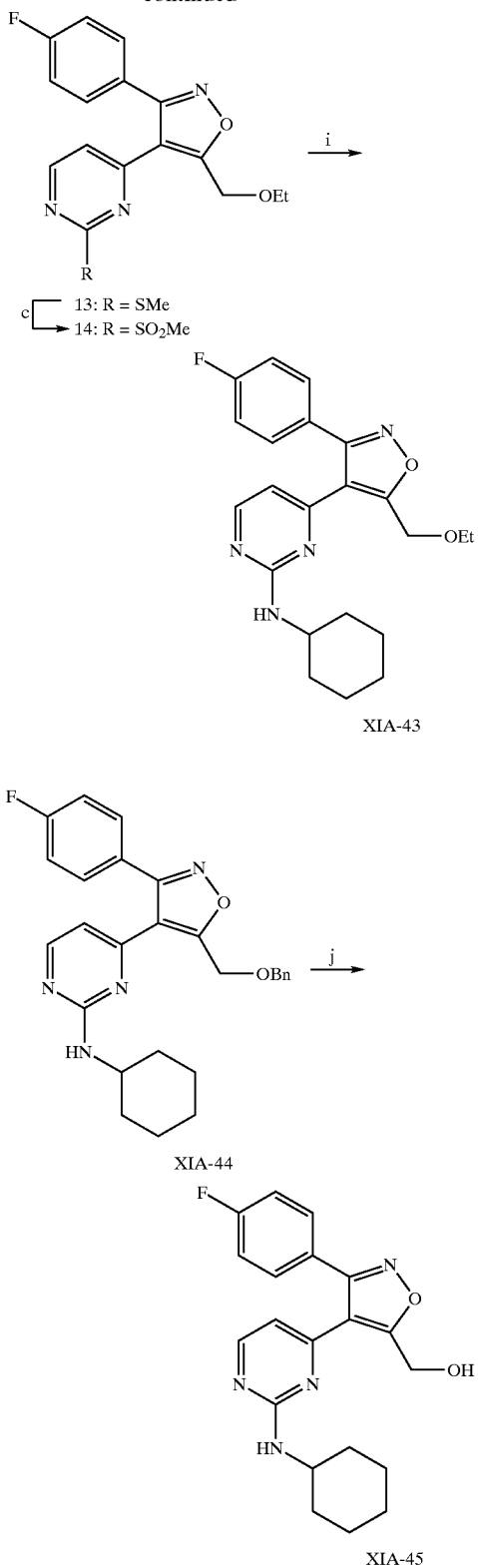

Reagents: (a) i. LDA, ii. 2-benzyloxy-N-methoxy-N-methyl-acetamide, −78° C. to rt; (b) Et₃N, EtOH, rt to reflux; (c) oxone; (d) iodotrimethylsilane; (e) PPh₃, CBr₄; (f) morpholine, Et₃N; (g) 4-aminocyclohexanol, DMSO, 80° C.; (h) NaOEt, EtOH; (i) cyclohexamine, DMSO, 80° C.; (j) 3:1 trifluoroacetic acid/H₂O; 100° C.

Reagents: (a) i. LDA, ii. 2-benzyloxy-N-methoxy-N-methyl-acetamide, −78° C. to rt; (b) Et₃N, EtOH, rt to reflux; (c) oxone; (d) iodotrimethylsilane; (e) PPh₃, CBr₄; (f) morpholine, Et₃N; (g) 4-aminocyclohexanol, DMSO, 80° C.; (h) NaOEt, EtOH; (i) cyclohexylamine, DMSO, 80° C.; (j) 3:1 trifluoroacetic acid/H₂O; 100° C.

Scheme II above shows a route for making isoxazoles of this invention where Q is a pyrimidine ring and $R^2$ is modified by various groups.

Scheme III

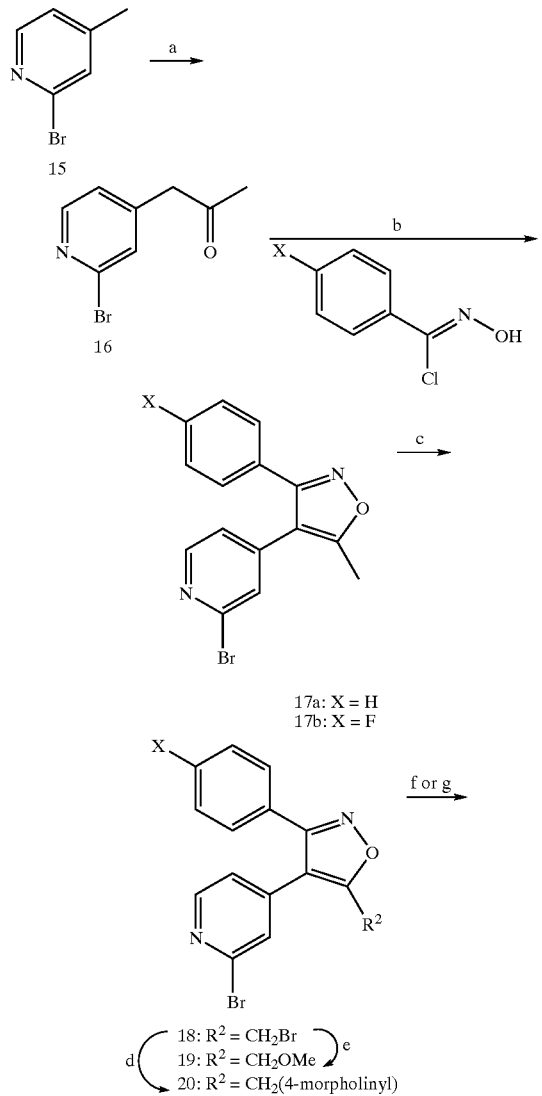

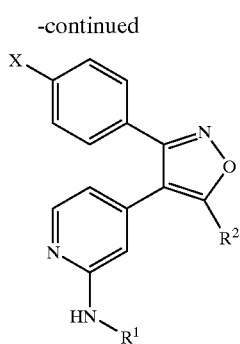

IIA-52: X = H, $R^1$ = phenyl, $R^2$ = $CH_3$
XIA-29: X = F, $R^1$ = cyclohexyl, $R^2$ = $CH_2OMe$ Reagents: (a) i. LDA, ii. N-methoxy-N-methyl-acetamide, -78° C. to rt; (b) Et₃N, EtOH, rt to reflux; (c) N-bromosuccinimide, AIBN, CCl₄, reflux; (d) morpholine, K₂CO₃, DMF; (e) NaOMe, MeOH; (f) aniline, Pd₂(dba)₃, BINAP, NaOtBu, toluene, 80° C.; (g) cyclohexylamine, Pd₂(dba)₃, BINAP, NaOtBu, toluene, 80° C.

Scheme III above shows a synthetic route for making isoxazoles of this invention where Q is a pyridine and $R^2$ is modified by various groups. In Scheme II and Scheme III, the isoxazole ring is first constructed and then the 2-position of the pyrimidine or pyridine ring is elaborated with the appropriate $NHR^1$ substitution. It will be apparent to one skilled in the art that position 2 of the pyrimidine or pyridine ring can be elaborated with the appropriate $NHR^1$ substitution before the isoxazole ring is constructed. Accordingly, isoxazoles of this invention may be obtained by performing step (b) using an appropriate intermediate having the formula XII:

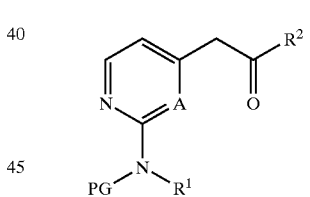

XII where A is N or CH; $R^1$ and $R^2$ are as described above; and PG is hydrogen or a nitrogen protecting group. Nitrogen protecting groups are well-known and include groups such as benzyl or $CO_2R$, where R is preferably alkyl, allyl or benzyl.

Scheme IV

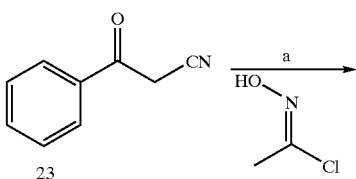

-continued
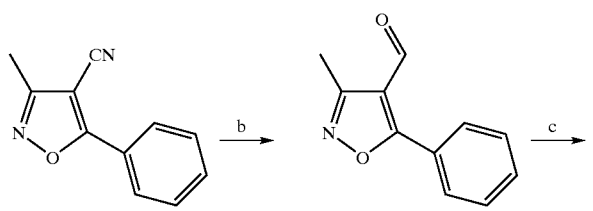
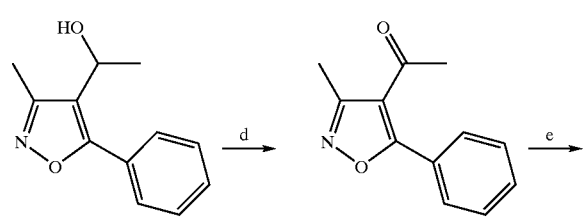
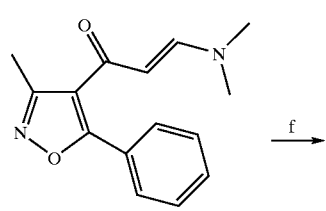
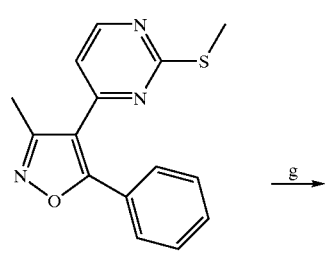
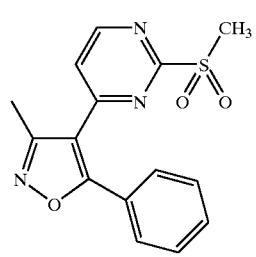
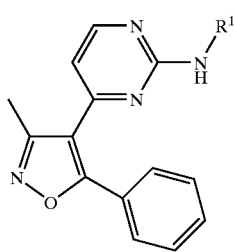
IB -continued Reagents: (a) Et₃N, EtOH; (b) DIBAL, toluene, 0° C.;
(c) CH₃MgBr, THF; (d) (COCl)₂, DMSO, Et₃N, CH₂Cl₂; (e)
DMF·DMA, toluene, reflux; (f) i. thiourea, MeONa,
MeOH, ii. pyridine, chloroform, CH₃I (g) m-CPBA,
CH₂Cl₂; (h) R¹NH₂, DMSO Scheme IV above shows a synthetic route for making reverse isoxazoles of this invention where Q is a pyrimidine ring.

Scheme V

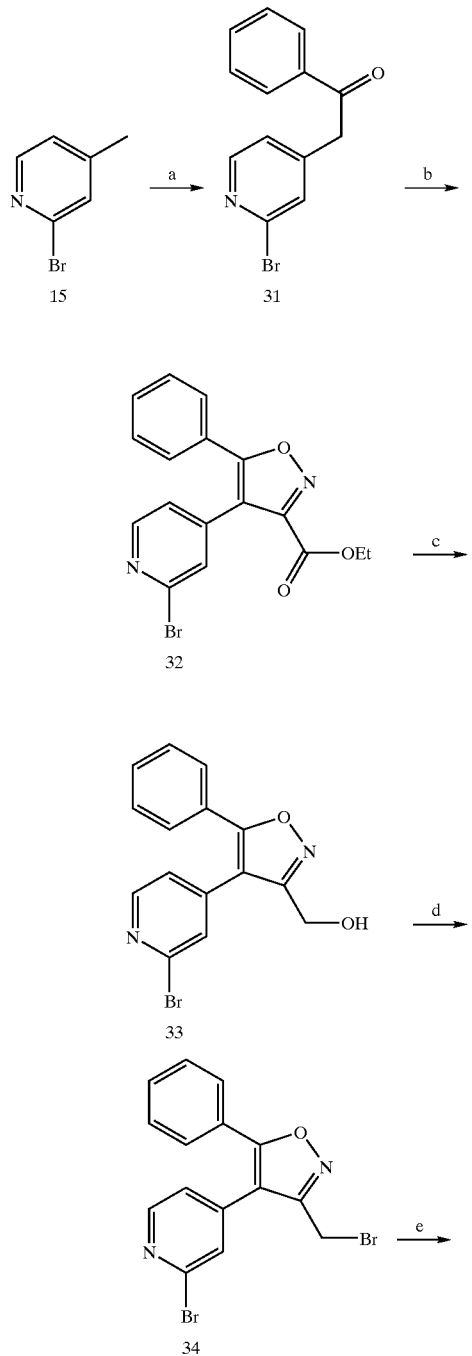

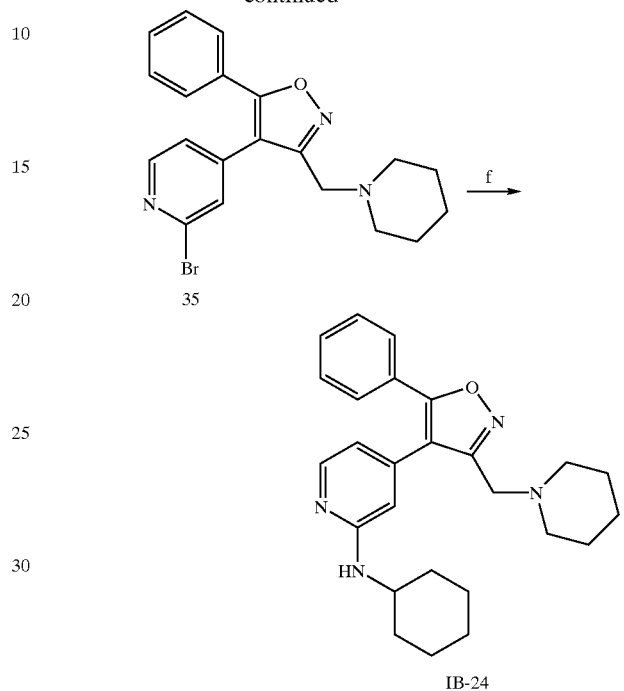

Reagents: (a) i. LDA, ii. N-methoxy-N-methylbenzamide; (b) Cl—C(=N—OH) CO₂Et, EtOH, Et₃N, 80° C.; (c) diisobutylaluminum hydride, CH₂Cl₂, room temperature; (d) PPh₃, CBr₄, CH₂Cl₂; (e) piperdine, K₂CO₃, DMF; (f) BINAP, Pd₂(dba)₃, NaOtBu, cyclohexylamine, toluene, 80° C.

Scheme V above shows a synthetic route for making reverse isoxazoles of this invention where Q is a pyridine ring.

Scheme VI

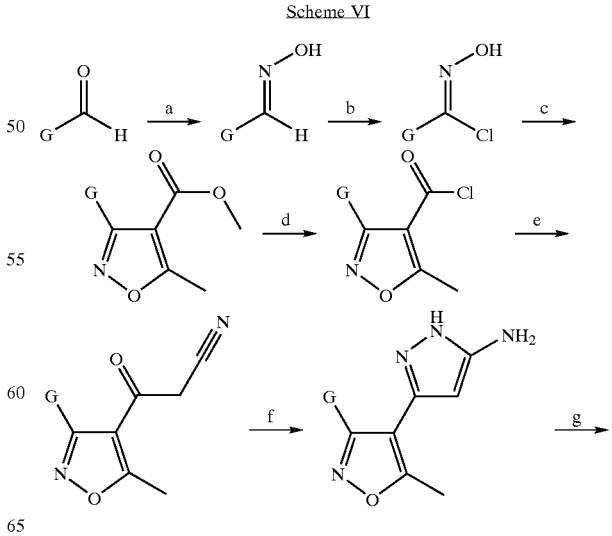

-continued

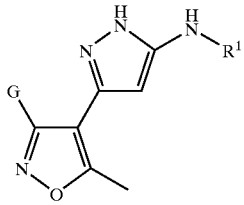

Reagents: a) NH₂OH/HCl, H₂O/EtOH; Na₂CO₃; (b) NCS, cat. pyridine, CH₂Cl₂; (c) CH₃COCH₂CO₂CH₃, Et₃N, EtOH; (d) i. NaOH, MeOH, H₂O; then, ii. SOCl₂, heat; (e) HO₂CCH₂CN, n-BuLi, -78 to 0° C.; (f) H₂NNH₂, EtOH; (g) R—X, dioxane.

Scheme VI above shows a general route for preparing compounds of this invention wherein Q is a pyrazole ring.

Scheme VII

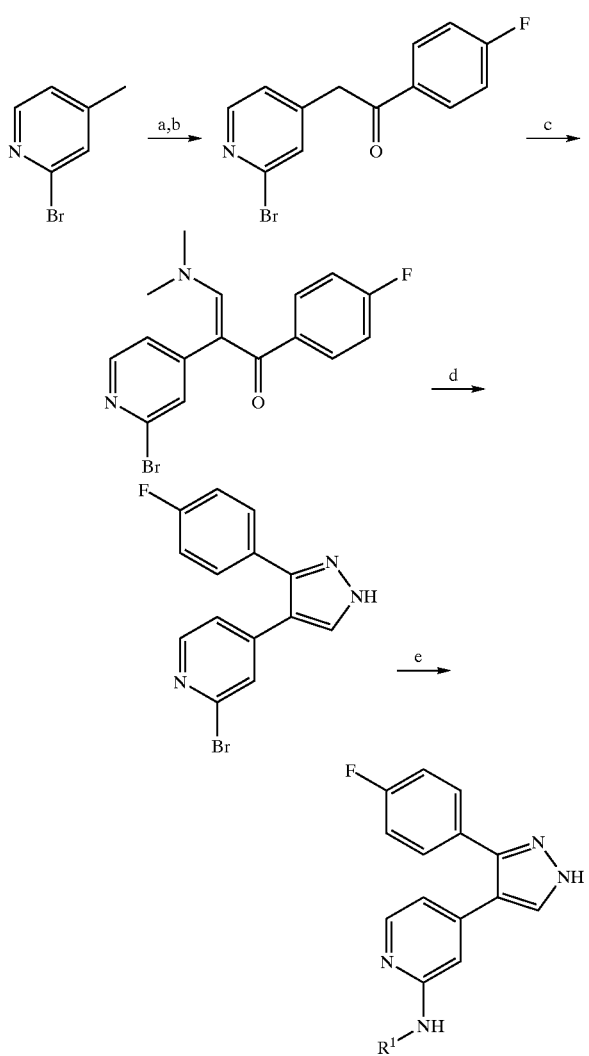

Reagents: (a) LDA, THF; (b) 4-F-C₆H₄CO₂Et; (c) DMF•DMA, toluene, reflux; (d) H₂NNH₂•H₂O, EtOH, reflux; (e) R¹NH₂, sealed tube, 140° C.

Scheme VII above shows a general route for preparing compounds of this invention wherein the XYZ ring is a pyrazole ring.

Certain of the intermediates that are useful for making the kinase inhibitors of this invention are believed to be novel.

Accordingly, one embodiment of this invention relates to compounds XII above and compounds represented by formula XIII:

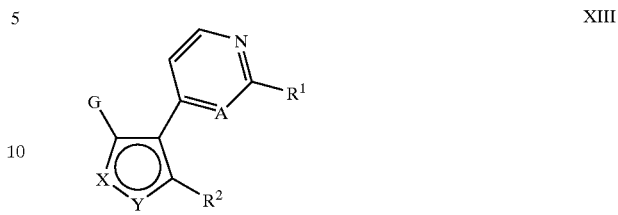

XIII wherein:
X—Y is N—O or O—N providing an isoxazole or reverse isoxazole ring;
A is N or CH;
G is R, aryl or substituted aryl;
R is aliphatic or substituted aliphatic
R² is selected from hydrogen, —R, —CH₂OR, —CH₂OH, —CH=O, —CH₂SR, —CH₂S(O)₂R, —CH₂(C=O)R, —CH₂CO₂R, —CH₂CO₂H, —CH₂CN, —CH₂NHR, —CH₂N(R)₂, —CH=N—OR, —CH=NNHR, —CH=NN(R)₂, —CH=NNHCOR, —CH=NNHCO₂R, —CH=NNHSO₂R, -aryl, -substituted aryl, —CH₂(aryl), —CH₂(substituted aryl), —CH₂NH₂, —CH₂NHCOR, —CH₂NHCONHR, —CH₂NHCON(R)₂, —CH₂NRCOR, —CH₂NHCO₂R, —CH₂CONHR, —CH₂CON(R)₂, —CH₂SO₂NH₂, —CH₂(heterocyclyl), —CH₂(substituted heterocyclyl), -(heterocyclyl), or -(substituted heterocyclyl); and
R¹ is selected from halogen, NH₂, SR, or SO₂R.

The activity of the JNK inhibitors of this invention may be assayed in vitro, in vivo or in a cell line. In vitro assays include assays that determine inhibition of either the kinase activity or ATPase activity of activated JNK. For example, see the testing examples described below. Alternate in vitro assays quantitate the ability of the inhibitor to bind to JNK and may be measured either by radiolabelling the inhibitor prior to binding, isolating the inhibitor/JNK complex and determining the amount of radiolabel bound, or by running a competition experiment where new inhibitors are incubated with JNK bound to known radioligands. One may use any type or isoform of JNK, depending upon which JNK type or isoform is to be inhibited.

The JNK inhibitors or pharmaceutical salts thereof may be formulated into pharmaceutical compositions for administration to animals or humans. These pharmaceutical compositions, which comprise an amount of JNK inhibitor effective to treat or prevent a JNK-mediated condition and a pharmaceutically acceptable carrier, are another embodiment of the present invention.

The term "JNK-mediated condition", as used herein means any disease or other deleterious condition in which JNK is known to play a role. Such conditions include, without limitation, inflammatory diseases, autoimmune diseases, destructive bone disorders, proliferative disorders, cancer, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2.

Inflammatory diseases which may be treated or prevented by the compounds of this invention include, but are not limited to, acute pancreatitis, chronic pancreatitis, asthma, allergies, and adult respiratory distress syndrome.

Autoimmune diseases which may be treated or prevented by the compounds of this invention include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated or prevented by the compounds of this invention include, but are not limited to, osteoporosis, osteoarthritis and multiple myeloma-related bone disorder.

Proliferative diseases which may be treated or prevented by the compounds of this invention include, but are not limited to, acute myelogenous leukemia, chronic myelogenous leukemia, metastatic melanoma, Kaposi's sarcoma, multiple myeloma and HTLV-1 mediated tumorigenesis.

Angiogenic disorders which may be treated or prevented by the compounds of this invention include solid tumors, ocular neovasculization, infantile haemangiomas. Infectious diseases which may be treated or prevented by the compounds of this invention include, but are not limited to, sepsis, septic shock, and Shigellosis.

Viral diseases which may be treated or prevented by the compounds of this invention include, but are not limited to, acute hepatitis infection (including hepatitis A, hepatitis B and hepatitis C), HIV infection and CMV retinitis.

Neurodegenerative diseases which may be treated or prevented by the compounds of this invention include, but are not limited to, Alzheimer's disease, Parkinson's disease, amyotrophic lateral sclerosis (ALS), epilepsy, seizures, Huntington's disease, traumatic brain injury, ischemic and hemorrhaging stroke, cerebral ischemias or neurodegenerative disease, including apoptosis-driven neurodegenerative disease, caused by traumatic injury, acute hypoxia, ischemia or glutamate neurotoxicity.

"JNK-mediated conditions" also include ischemia/reperfusion in stroke, heart attacks, myocardial ischemia, organ hypoxia, vascular hyperplasia, cardiac hypertrophy, hepatic ischemia, liver disease, congestive heart failure, pathologic immune responses such as that caused by T cell activation and thrombin-induced platelet aggregation.

In addition, JNK inhibitors of the instant invention may be capable of inhibiting the expression of inducible pro-inflammatory proteins. Therefore, other "JNK-mediated conditions" which may be treated by the compounds of this invention include edema, analgesia, fever and pain, such as neuromuscular pain, headache, cancer pain, dental pain and arthritis pain.

The compounds of this invention are also useful as inhibitors of Src-family kinases, especially Src and Lck. For a general review of these kinases see Thomas and Brugge, Annu. Rev. Cell Dev. Biol. (1997) 13, 513; Lawrence and Niu, Pharmacol. Ther. (1998) 77, 81; Tatosyan and Mizenina, Biochemistry (Moscow) (2000) 65, 49. Accordingly, these compounds are useful for treating diseases or conditions that are known to be affected by the activity of one or more Src-family kinases. Such diseases or conditions include hypercalcemia, restenosis, hypercalcemia, osteoporosis, osteoarthritis, symptomatic treatment of bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obtructive pulmonary disorder, contact dermatitis, cancer, Paget's disease, asthma, ischemic or reperfusion injury, allergic disease, atopic dermatitis, and allergic rhinitis. Diseases that are affected by Src activity, in particular, include hypercalcemia, osteoporosis, osteoarthritis, cancer, symptomatic treatment of bone metastasis, and Paget's disease. Diseases that are affected by Lck activity, in particular, include autoimmune diseases, allergies, rheumatoid arthritis, and leukemia. Compounds of formula II-A and I-B wherein $Ar^2$ is aryl are especially useful for treating diseases associated with the Src-family kinases, particularly Src or Lck.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of JNK inhibitor that may be combined with the carrier materials to produce a single dosage form will vary depending upon the host treated, the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a JNK-mediated condition comprising the step of administering to a patient one of the above-described pharmaceutical compositions. The term "patient", as used herein, means an animal, preferably a human.

Preferably, that method is used to treat or prevent a condition selected from inflammatory diseases, autoimmune diseases, destructive bone disorders, proliferative disorders, infectious diseases, degenerative diseases, neurodegenerative diseases, allergies, reperfusion/ischemia in stroke, heart attacks, angiogenic disorders, organ hypoxia, vascular hyperplasia, cardiac hypertrophy, and thrombin-induced platelet aggregation, or any specific disease or disorder described above.

Depending upon the particular JNK-mediated condition to be treated or prevented, additional drugs, which are normally administered to treat or prevent that condition, may be administered together with the inhibitors of this invention. For example, chemotherapeutic agents or other anti-proliferative agents may be combined with the JNK inhibitors of this invention to treat proliferative diseases.

Those additional agents may be administered separately, as part of a multiple dosage regimen, from the JNK inhibitor-containing composition. Alternatively, those agents may be part of a single dosage form, mixed together with the JNK inhibitor in a single composition.

In order that the invention described herein may be more fully understood, the following examples are set forth. It should be understood that these examples are for illustrative purposes only and are not to be construed as limiting this invention in any manner.

EXAMPLE 1
Benzaldehyde Oxime.

To benzaldhyde (10.0 g, 94 mmol) in ethanol (50 mL) was added hydroxylamine hydrochloride (6.5 g, 94 mmol in $H_2O$ (50 mL) followed by $Na_2CO_3$ in $H_2O$ (50 mL). Reaction solution was stirred for 2 hr. Poured into brine and extracted twice with diethyl ether. Combined extracts were dried over $MgSO_4$. Evaporation afforded benzaldehyde oxime (11.0 g, 96.5% yield) as a colorless oil. $^1H$ NMR ($CDCl_3$) δ 7.40–7.50 (m, 3H), 7.60–7.70 (m, 2H) 8.22 (s, 1H), 9.1 (bs, 1H).

EXAMPLE 2
α-Chlorobenzaldehyde Oxime (Benzoyl Chloride Oxime).

To benzaldehyde oxime (12.2 g, 0.1 mol) in chloroform was added catalytic amount of pyridine, followed by N-chlorosuccinimide (13.35 g, 0.1 mol) at room temperature. The reaction mixture was stirred for 1.5 h, then saturated aqueous NaCl was added. The organic phase was washed with saturated aqueous NaCl (twice) and dried with $MgSO_4$. The solvent was removed under reduced pressure. 13.85 g α-chlorobenzaldehyde oxime was obtained. The yield was 87%.

EXAMPLE 3
1-(5-Methyl-3-phenyl-isoxazol-4-yl)-ethanone (Compound 3).

To a solution of pentane-2,4-dione (13.23 g, 0.132 mol) and triethylamine (13.35 g, 0.132 mol) in ethanol was added α-chlorobenzaldehyde oxime (13.70 g, 0.088 mol) at room temperature. The reaction mixture was stirred overnight at room temperature. To the reaction was added ethyl acetate and saturated aqueous NaCl. The organic phase was washed with saturated aqueous NaCl (twice) and dried with $MgSO_4$, and the organic solvent was removed under reduced pressure to provide 17.7 g of the title compound. The yield was 100%.

EXAMPLE 4
4-(5-methyl-3-phenyl-isoxazol-4-yl)-pyrimidin-2-ylamine (Compound 5).

The above Compound 3 (17.7 g, 0.088 mol) and dimethylformamide dimethyl acetal (DMF.DMA) (160 g, 0.132 mol) were refluxed overnight. To the reaction mixture was added ethyl acetate and saturated aqueous NaCl. The organic phase was washed with saturated aqueous NaCl (twice) and dried ($MgSO_4$). The organic solvent was removed under reduced pressure, and the crude product material was dissolved in 200 mL methanol. To the solution was added guanidine hydrochloride (10.5 g, 0.110 mol) in 100 mL methanol, followed by sodium methoxide (6.17 g, 0.114 mol) in 100 mL methanol. The reaction mixture was refluxed overnight and then was cooled to room temperature. The reaction solvent was concentrated to approximately 100 mL total volume, and the precipitated product was filtered. The filtration cake afforded the title compound (9.3 g). The overall yield for two steps was 46%.

EXAMPLE 5
[4-(5-Methyl-3-phenyl-isoxazol-4-yl)-pyrimidin-2-yl]-phenyl-amine (Compound IIA).

To a solution of 50 mg (0.2 mmol) of 4-(5-methyl-3-phenyl-isoxazole-4-yl)-pyrimidin-2-ylamine in 1 mL of toluene was added successively 63 μL (0.6 mmol) of bromobenzene, 10 mg of tris(dibenzylideneacetone) dipalladium, 10 mg of BINAP and 39 mg (0.4 mmol) of sodium tert-butoxide. The mixture was heated at reflux for 16 h, diluted with ethyl acetate, filtered, washed successively with saturated aqueous sodium bicarbonate and brine, dried ($MgSO_4$) and concentrated in vacuo. The residue was purified by column chromatography over silica gel eluted with ethyl acetate-hexanes 1:3, to afford 24 mg (36%) of the title compound as a yellow oil.

EXAMPLE 6
5-Methyl-3-phenyl-isoxazole-4-carboxylic Acid Methyl Ester.

An ethanol solution of freshly prepared benzoyl chloride oxime (14.0 g, 90 mmol) (100 mL) was added dropwise, at 5° C. to methyl acetoacetate (11.18 g, 96 mmol) and triethyl amine (13 mL, 103 mmol) in ethanol (50 ml). After stirring for 12 hr at ambient temperature, the solution was diluted with $CH_2Cl_2$, washed with 1N HCl. saturated $NaHCO_3$, brine, dried over $MgSO_4$ and evaporated to give amber oil. Flash chromatography (silica) with 10% ethyl acetate in hexanes afforded the title compound (7.56 g, 39% yield) as a white solid: MS m/z MH+218 (100); $^1H$ NMR ($CDCl_3$) δ 2.78 (s, 3H), 3.81 (s, 3H), 7.45–7.55 (m, 3H), 7.65–7.69 (m, 2H).

EXAMPLE 7
5-Methyl-3-phenyl-isoxazole-4-carboxylic Acid.

To 5-Methyl-3-phenyl-isoxazole-4-carboxylic acid methyl ester (0.853 g, 3.69 mmol) in methanol (12 mL) was added 2N NaOH (8 mL) the reaction solution was stirred at ambient temperature for 60 hr. The solution was dilute with water and extracted twice with ethyl acetate. The combined extract was washed with brine and dried over $MgSO_4$ and concentrated. Recrystallization (hexanes/ethyl acetate) afforded a white solid (0.540 g, 72% yield).

EXAMPLE 8
5-Methyl-3-phenyl-isoxazole-4-carbonyl Chloride.

5-Methyl-3-phenyl-isoxazole-4-carboxylic acid (0.54 g, 2.56 mmol) was treated with $SOCl_2$ (2 mL) at 70° C. for 1 hr. Concentration in vacuum gave a yellow oil which was used without purification.

EXAMPLE 9
3-(5-Methyl-3-phenyl-isoxazol-4-yl)-3-oxo-propionitrile.

To cyanoacetic acid (0.43 g, 5.12 mmol) in THF at −78° C., containing one crystal of 1,1'-bipyridyl was added n-butyl lithium (6.4 mL, 10.24 mmol). The temperature was allowed to warm to 0° C. resulting in a pink colored solution. After cooling to −78° C., 5-Methyl-3-phenyl-isoxazole-4-carbonyl chloride (0.567 g, 2.56 mmol) in THF (5 mL) was added dropwise. The mixture was stirred at −78° C. for 1 hr. and at ambient temperature for an addition 1 hr. The reaction was quenched with 1N HCl (13 mL0 and extracted twice with $CH_2Cl_2$. Combined extracts were washed with saturated NaHCO$_3$, brine, dried over MgSO$_4$ to give the title compound (0.391 g, 67% yield).

EXAMPLE 10
N-[5-(5-Methyl-3-phenyl-isoxazol-4-yl)-2H-pyrazol-3-yl]-benzamide.

3-(5-Methyl-3-phenyl-isoxazol-4-yl)-3-oxo-propionitrile (0.391 g, 1.73 mmol) in Ethanol (3 mL) was treated with hydrazine (0.168 mL, 3.46 mmol) and heated to reflux. Evaporation in vacuum gave 5-(5-Methyl-3-phenyl-isoxazol-4-yl)-2H-pyrazol-3-ylamine used without purification. To the resulting amine (0.039 g, 0.16 mmol) in dioxane was added triethyl amine followed by benzyl chloride (0.019 mL, 0.16 mmol). The reaction was stirred at 10° C. for 1 hr and 2 hr at ambient temperature. The solution was diluted with water extracted with ethyl acetate, washed with saturated NaHCO$_3$, Brine, dried over MgSO$_4$ and concentrated in vacuum. HPLC purification afforded 1.4 mg of title compound.

EXAMPLE 11
1-Benzyloxy-3-(2-methylsulfanylpyrimidin-4-yl)-propan-2-one (Compound 7).

To a stirred solution of 4-methyl-2-methylsulfanylpyrimidine (9.60 g, 68.5 mmol) in THF (150 mL) at −78° C. was added LDA (2.0 M THF/Hex, 41.1 mL, 82.2 mmol) dropwise over 10 min. The solution was stirred at −78° C. for 15 minutes, warmed to 0° C. for 10 minutes and recooled to −78° C. for 15 minutes. Then, a solution of 3-benzyloxy-N-methyl-N-methoxyacetamide (17.2 g, 82.2 mmol) in THF (30 mL) was added dropwise over 45 minutes. After 15 min. at −78° C., the solution was warmed to 0° C. and stirred for 30 min. The reaction was quenched with HCl (1M, 85 mL) and stirred for 1 h. The solution was poured into saturated NaHCO$_3$ (300 mL), extracted with Et$_2$O (3×200 mL), dried (MgSO$_4$), filtered and concentrated. Flash chromatography (SiO$_2$, 20% EtOAc-hexanes) provided the title compound (13.75 g, 47.7 mmol, 69% yield).

EXAMPLE 12
4-[5-Benzyloxymethyl-3-(4-fluoro-phenyl)-isoxazol-4-yl]-2-methylsulfanyl-pyrimidine (Compound 8).

To a stirred solution of the above compound 7 (13.75 g, 47.7 mmol) and Et$_3$N (14.6 mL, 105 mmol) in EtOH (200 mL), was added a solution of 4-fluoro-benzoylchloride oxime (56 mmol) in EtOH (50 mL) over 30 min. The solution was stirred at 25° C. for 15 min. Then, the solution was heated to reflux for 90 min. The solution was cooled to 25° C. Additional Et$_3$N (7.3 mL, 52 mmol) was added followed by dropwise addition of a solution of 4-fluoro-benzoylchloride oxime (38.5 mmol) in EtOH (50 mL) over 1 h. to drive the reaction to completion. The solution was refluxed for 1 h. until TLC indicated that all of the starting isoxazole was consumed. The solution was cooled to 25° C. and concentrated. The crude material was picked up in CH$_2$Cl$_2$ (50 mL) and poured into saturated aqueous NaHCO$_3$ (150 mL), extracted with CH$_2$Cl$_2$ (3×150 mL), dried (MgSO$_4$), filtered and concentrated. Flash chromatography (SiO$_2$, 20% EtOAc-hexanes) provided the title compound (14.2 g, 34.8 mmol, 60%) in sufficient purity (>85%) for use in the next reaction.

EXAMPLE 13
4-[5-Benzyloxymethyl-3-(4-fluoro-phenyl)-isoxazol-4-yl]-2-methanesulfonyl-pyrimidine (Compound 9).

To a stirred solution of the above compound 8 (2.00 g, 4.91 mmol) in MeOH (50 mL) at 25° C. was added dropwise a solution of oxone (7.07 g, 11.5 mmol) in H$_2$O (50 mL) over 10 min. After 20 h., the solution was poured into H$_2$O (75 mL), extracted with CH$_2$Cl$_2$ (3×75 mL), dried (MgSO$_4$), filtered and concentrated. Flash chromatography (SiO$_2$, 45% EtOAc-hexanes) provided the title compound (1.60 g, 3.64 mmol, 74%).

EXAMPLE 14
[3-(4-Fluoro-phenyl)-4-(2-methanesulfonyl-pyrimidin-4-yl)-isoxazol-5-yl]-methanol (Compound 10).

To a stirred solution of the above compound 9 (750 mg, 1.70 mmol) in CHCl$_3$ (8.5 mL) at 0° C. was added trimethylsilyl iodide (0.73 mL, 5.1 mmol). The reaction was stirred at 0° C. for 30 min. Then, additional trimethylsilyl iodide (0.48 mL, 3.4 mmol) was added. After 40 min. the solution was warmed to 25° C. and stirring was continued for 22 h. The solution was quenched with H$_2$O—MeOH (2 mL) and stirred for 1 h. The solution was poured into saturated aqueous NaHCO$_3$ (30 mL), extracted with EtOAc (3×30 mL), and concentrated. Flash chromatography (SiO$_2$, 80% EtOAc-hexanes) provided the title compound (530 mg, 1.52 mmol, 89%).

EXAMPLE 15
4-[5-(Bromomethyl)-3-(4-fluoro-phenyl)-isoxazol-4-yl]-2-methanesulfonyl-pyrimidine (Compound 11).

To a stirred solution of the above compound 10 (250 mg, 0.716 mmol) and CBr$_4$ (473 mg, 1.43 mmol) in CH$_2$Cl$_2$ (14 mL) at 25° C. was added PPh$_3$ (244 mg, 0.93 mmol). After 10 min., additional PPh$_3$ (50 mg, 0.19 mmol) was added to drive the reaction to completion. After 15 min., the solution was concentrated. Flash chromatography (SiO$_2$, 50% EtOAc-hexanes) provided the title compound (265 mg, 0.643 mmol, 90%).

EXAMPLE 16
4-[3-(4-Fluoro-phenyl)-4-(2-methanesulfonyl-pyrimidin-4-yl)-isoxazol-5-ylmethyl]-morpholine (Compound 12).

To a stirred solution of the above compound 11 (41 mg, 0.099 mmol) and Et$_3$N (20 μL, 0.15 mmol) in CH$_3$CN (0.5 mL) at 25° C. was added morpholine (9.6 μL, 0.11 mmol). After 15 min. the solution was concentrated. Preparative thin layer chromatography is 15 (SiO$_2$, EtOAc) provided the title compound (29 mg, 0.069 mmol, 70%).

EXAMPLE 17
4-{4-[3-(4-Fluoro-phenyl)-5-(morpholin-4-ylmethyl)-isoxazol-4-yl]pyrimidin-2-ylamino}cyclohexanol (Compound XIA-42).

A stirred solution of Compound 13 (29 mg, 0.069 mmol) and trans-4-aminocyclohexanol (24 mg, 0.21 mmol) in DMSO (0.21 mL) was heated to 80° C. for 4 h. The solution was poured into half-saturated aqueous NaHCO$_3$ (5 mL), extracted with EtOAc (5×5 mL), dried (MgSO$_4$), filtered and concentrated. Flash chromatography (SiO$_2$, 10% MeOH—CH$_2$Cl$_2$) provided material which was further purified by ion exchange chromatography (SCX resin, eluent: 0.25M NH$_3$ in 50% MeOH—CH$_2$Cl$_2$) to give the title compound (27 mg, 0.057 mmol, 83%).

EXAMPLE 18
4-[5-Ethoxymethyl-3-(4-fluoro-phenyl)-isoxazol-4-yl]-2-methylsulfanyl-pyrimidine (Compound 13).

To a stirred solution of the above compound 8 (103 mg, 0.27 mmol) in EtOH (2.0 mL) at 25° C. was added NaOEt (21% w/v EtOH, 0.40 mL, 1.23 mmol). After 2 h. the reaction was quenched with saturated aqueous NH$_4$Cl (3 mL), CH$_2$Cl$_2$ (3×5 mL), dried (MgSO$_4$), filtered and concentrated. Flash chromatography (SiO$_2$, 25% EtOAc-hexanes) provided the title compound (58 mg, 0.17 mmol, 62%).

EXAMPLE 19
4-[5-Ethoxymethyl-3-(4-fluoro-phenyl)-isoxazol-4-yl]-2-methanesulfonyl-pyrimidine (Compound 14).

This compound was prepared in a manner similar to that described above in Example 13, except starting from the above compound 13 (58 mg, 0.17 mmol) to provide the title compound (64 mg, 0.17 mmol, 100%) which was used directly in the next reaction without purification or characterization.

EXAMPLE 20
Cyclohexyl-{4-[5-ethoxymethyl-3-(4-fluoro-phenyl)-isoxazol-4-yl]-pyrimidin-2-yl}amine (Compound XIA-43)

This compound was prepared in a manner similar to that described above in Example 17, starting from the above compound 14 (64 mg, 0.17 mmol) and cyclohexylamine (58 $\mu$L, 0.51 mmol) to provide the title compound as crude product. After HPLC purification (C-18, gradient elution, 10–90% $H_2O$—$CH_3CN$) and extraction into EtOAc, the crude product was converted to the HCl salt with HCl-$Et_2O$ (1M, 1 mL). The solvents were removed in vacuo the give the title compound as the HCl salt (55 mg, 0.13 mmol, 76% over two steps from compound 13).

EXAMPLE 21
Cyclohexyl-{4-[5-benzyloxymethyl-3-(4-fluoro-phenyl)-isoxazol-4-yl]-pyrimidin-2-yl}amine (Compound XIA-44)

This compound was prepared in a manner similar to that described above in Example 17 starting from the above compound 9 (500 mg, 1.14 mmol) and cyclohexylamine (340 $\mu$L, 3.42 mmol). Flash chromatography ($SiO_2$, 30% EtOAc-hexanes) provided the title compound (488 mg, 1.06 mmol, 93%).

EXAMPLE 22
[4-(2-Cyclohexylamino-pyrimidin-4-yl)-3-(4-fluoro-phenyl)-isoxazol-5-yl]methanol (Compound XIA-45)

A stirred solution of the above compound XIA-44 (461 mg, 1.01 mmol) in TFA-$H_2O$ (3:1, 8 mL) was heated to 80° C. for 20 h. The solution was concentrated, and the crude mixture was taken up in $CH_2Cl_2$ (25 mL), poured into saturated aqueous $NaHCO_3$ (30 mL), extracted with $CH_2Cl_2$ (3×25 mL), dried ($MgSO_4$), filtered and concentrated. TLC (50% EtOAc-hexanes) indicated about 50% consumption of starting compound XIA-44. The crude material was dissolved in TFA-$H_2O$ (3:1, 8 mL) and the resulting solution was heated to 100° C. for 22 h. The solution was concentrated, and the crude mixture was taken up in $CH_2Cl_2$ (25 mL), poured into saturated aqueous $NaHCO_3$ (30 mL), extracted with $CH_2Cl_2$ (3×25 mL), dried ($MgSO_4$), filtered and concentrated. Flash chromatography ($SiO_2$, 40% EtOAc-hexanes) provided the title compound (313 mg, 0.85 mmol, 84%).

EXAMPLE 23
1-(2-Bromo-pyridin-4-yl)-propan-2-one (Compound 16).

To a stirred solution of 2-bromo-4-methylpyridine (Compound 15) (20.20 g, 117.4 mmol) in THF (250 mL) at −78° C. was added LDA (2.0 M THF/Hex, 70.5 mL, 141 mmol) dropwise over 10 min. The solution was stirred at −78° C. for 35 min. Then a solution of N-methoxy-N-methyl acetamide (14.5 g, 141 mmol) in THF (30 mL) was added dropwise over 10 min. After 15 min. at −78° C., the solution was warmed to 0° C. and stirred for 1 h. The solution was poured into $H_2O$ (250 mL), extracted with $Et_2O$ (3×250 mL), dried ($MgSO_4$), filtered and concentrated. Flash chromatography ($SiO_2$, 20% EtOAc-hexanes) provided the title compound (16.75 g, 78.2 mmol, 67%).

EXAMPLE 24
2-Bromo-4-(5-methyl-3-phenyl-isoxazol-4-yl)-pyridine (Compound 17a).

To a stirred solution of Compound 16 (1.71 g, 8.0 mmol) and $Et_3N$ (2.23 mL, 16 mmol) in EtOH (16 mL) was added a solution of benzoylchloride oxime (1.62 g, 10.4 mmol) in EtOH (16 mL) over 90 min. The solution was stirred at 25° C. for 90 min. Then, the solution was heated to reflux for 24 h. The solution was cooled to 25° C. and concentrated. The crude material was taken up in $CH_2Cl_2$ (50 mL) and poured into saturated aqueous $NaHCO_3$ (50 mL), extracted with $CH_2Cl_2$ (3×50 mL), dried ($Na_2SO_4$), and filtered. Flash chromatography ($SiO_2$, 20% EtOAc-hexanes) provided the title compound (1.32 g, 4.19 mmol, 52%).

2-Bromo-4-[3-(4-fluoro-phenyl)-5-methyl-isoxazol-4-yl]-pyridine (Compound 17b) was similarly prepared starting with 4-fluorobenzoylchloride oxime.

EXAMPLE 25
2-Bromo-4-(5-bromomethyl-3-phenyl-isoxazol-4-yl)-pyridine (Compound 18a).

A stirred solution of the above Compound 17a (404 mg, 1.28 mmol), N-bromosuccinimide (239 mg, 1.35 mmol) and AIBN (11 mg, 0.064 mmol) in $CCl_4$ (3 mL) was heated to reflux and placed under a 300 W lamp for 18 h. The solution was diluted with $CH_2Cl_2$ (15 mL), extracted with $H_2O$ (3×10 mL), brine (40 mL), dried ($MgSO_4$), filtered and concentrated. Flash chromatography ($SiO_2$, 15–20% EtOAc-hexanes) provided the title compound (287 mg, 0.728 mmol, 57%).

2-Bromo-4-[5-bromomethyl-3-(4-fluoro-phenyl)-isoxazol-4-yl]-pyridine (Compound 18b) was similarly prepared starting with Compound 17b.

EXAMPLE 26
2-Bromo-4-(5-methoxymethyl-3-(4-fluoro-phenyl)-isoxazol-4-yl)-pyridine (Compound 19b).

To the above Compound 18b (200 mg, 0.485 mmol) was added NaOMe (0.5 M in MeOH, 2.0 mL, 1.0 mmol). The solution was stirred at 25° C. for 90 min. Then, the solution was poured into brine, extracted with EtOAc (4×15 mL), dried ($MgSO_4$), filtered through a silica plug. Evaporation of the solvent provided the title compound (175 mg, 0.482 mmol, 99%).

EXAMPLE 27
4-(4-(2-Bromo-pyridin-4-yl)-3-phenyl-isoxazol-5-ylmethyl)-morpholine (Compound 20a).

A stirred solution of the above Compound 18a (484 mg, 1.22 mmol), morpholine (0.45 mL, 5.1 mmol) and $K_2CO_3$ (340 mg, 2.45 mmol) in anhydrous DMF (2 mL) was warmed to 40° C. for 18 h. The solution was poured into brine (10 ml), extracted with $CH_2Cl_2$ (3×15 mL), dried ($MgSO_4$), and filtered. Flash chromatography ($SiO_2$, 50% EtOAc-hexanes) provided the title compound (461 mg, 1.15 mmol, 94%).

EXAMPLE 28
[4-(5-Methyl-3-phenyl-isoxazol-4-yl)-pyridin-2-yl]phenyl-amine (Compound IIA-52).

To a stirred solution of the above Compound 17a (20 mg, 0.063 mmol), aniline (7.0 $\mu$L, 0.076 mmol) and BINAP (5.6 mg, 0.009 mmol) in toluene (0.6 mL) at 25° C. was added $Pd_2(dba)_3$ (2.7 mg, 0.003 mmol) followed by NaOtBu (9.1 mg, 0.095 mmol). The solution was heated to 80° C. for 2 h. The solution was cooled, filtered and concentrated. Preparative thin layer chromatography ($SiO_2$, 5% EtOAc/$CH_2Cl_2$) provided the title compound (12.6 mg, 0.0385 mmol, 61%).

EXAMPLE 29

Cyclohexyl-[4-(5-methoxymethyl-3-(4-fluoro-phenyl)-isoxazol-4-yl)-pyridin-2-yl]-amine (Compound XIA-29).

To a stirred solution of the above Compound 19b (20 mg, 0.050 mmol), cyclohexylamine (11 μL, 0.13 mmol), and BINAP (4.7 mg, 0.0075 mmol) in toluene (0.4 mL) at 25° C. was added $Pd_2(dba)_3$ (2.3 mg, 0.0025 mmol) followed by NaOtBu (12 mg, 0.13 mmol). The solution was heated to 80° C. for 15 h. The solution was cooled, poured into $H_2O$ (5 mL), extracted with EtOAc (4×5 mL), dried ($MgSO_4$), filtered and concentrated. HPLC (gradient elution, 90-10% $H_2O$—$CH_3CN$) provided the title compound (9.1 mg, 0.022 mmol, 44%).

EXAMPLE 30

3-Methyl-5-phenyl-isoxazole-4-carbonitrile (Compound 24).

To an ethyl alcohol solution of benzoylacetonitrile was added 1.5 eq of triethyl amine, followed by 1.5 eq of acetylchloride oxime, the reaction mixture was stirred at r.t. for 4 hours. To the reaction mixture was added ethyl acetate and brine. The organic phase was dried with magnesium sulfate and the solvent was removed under reduced pressure. After chromatographic purification the title compound was obtained in 72% yield.

EXAMPLE 31

3-Methyl-5-phenyl-isoxazole-4-carbaldehyde (Compound 25).

To a toluene solution of the above compound 24 was added 1.2 eq of DIBAL-H/HAX at 0° C. The reaction was stirred at 0° C. for 3 hours, allowed to warm to room temperature and was stirred at r.t. overnight. The reaction mixture was transfered to 1N HCl slowly and then extracted with ethyl acetate. The organic phase was dried over magnesium sulfate and concentrated under reduced pressure. The crude product was purified by chromatograph providing the title compound in 57% yield.

EXAMPLE 32

1-(3-Methyl-5-phenyl-isoxazol-4-yl)-ethanol (Compound 26).

To the THF solution of the above Compound 25 was slowly added 1.4 eq of methylmagnesium bromide at room temperature. The reaction mixture was stirred at r.t. for 1 h. To the reaction mixture was added ethyl acetate and 1N HCl. The organic phase was washed with brine and dried over magnesium sulfate. The solvent was removed under reduced pressure, and the crude product, obtained in 96% yield, was used directly for the next step without purification.

EXAMPLE 33

1-(3-Methyl-5-phenyl-isoxazol-4-yl)-ethanone (Compound 27).

To a dichloromethane solution of oxalyl chloride was added DMSO at −78° C., the mixture was stirred at −78° C. for 15 min and followed by addition of a dichloromethane solution of compound the above Compound 26. The reaction mixture was stirred for 30 min at −78° C., then triethylamine was added, after which the reaction mixture was allowed to warm to room temperature gradually. To the reaction mixture was added ethyl acetate and brine. The organic phase was dried over magnesium sulfate, and the solvent was removed under reduced pressure. The crude product, obtained in 94% yield, was used directly for the next step without purification.

EXAMPLE 34

3-Dimethylamino-1-(3-methyl-5-phenyl-isoxazol-4-yl)-propenone (Compound 28).

A toluene solution of the above Compound 27 and excess DMF-DMA was refluxed for 20 hours. To the reaction mixture was added ethyl acetate and brine, the organic phase was dried over magnesium sulfate, and the solvent was then removed under reduced pressure. The crude product was used for the next step without purification.

EXAMPLE 35

4-(3-Methyl-5-phenyl-isoxazol-4-yl)-2-methylsulfanyl-pyrimidine (Compound 29).

A methanol suspension of the above Compound 28, 2 equivalents of thiourea and 1.5 equivalents of sodium methoxide was refluxed for 2 days. To the reaction mixture was added ethyl acetate and 1N HCl, the organic phase was washed with brine and dried over magnesium sulfate, and the solvent was then removed under reduced pressure. The crude product was dissolved in chloroform, to it was added 1.5 eq of iodomethane and 1.5 eq of pyridine. The reaction mixture was stirred at r.t. for 2 hours. To the reaction mixture was added dichloromethane and 1N HCl, the organic phase was washed with brine and dried with magnesium sulfate. The solvent was removed under reduced pressure, and the crude product was purified by chromatography to provide the title compound. The yield was 32%.

EXAMPLE 36

4-(3-Methyl-5-phenyl-isoxazol-4-yl)-2-methanesulfonyl-pyrimidine (Compound 30).

To a dichloromethane solution of the above Compound 29 was added 2 eq of m-CPBA, and the reaction was stirred at r.t. for overnight. The reaction mixture was washed with 1N NaOH twice and brine twice and dried with magnesium sulfate. The solvent was removed under reduced pressure and the crude product was purified by chromatograph to provide the title compound in 79% yield.

EXAMPLE 37

Compounds IB.

A DMSO solution of the above Compound 30 and 3 equivalents of desired amine was heated at 80° C. for 4 hours. After analytical HPLC indicated the reaction was completed, the crude product was purified by reversed HPLC to provide the desired Compound IB. The yield is generally greater than 80%.

The following examples demonstrate how the compounds of this invention may be tested as protein kinase inhibitors, especially inhibitors of c-Jun-N-terminal kinases.

EXAMPLE 38

Cloning, Expression and Purification of JNK3 Protein

A BLAST search of the EST database using the published JNK3α1 cDNA as a query identified an EST clone (#632588) that contained the entire coding sequence for human JNK3α1. Polymerase chain reactions (PCR) using pfu polymerase (Strategene) were used to introduce restriction sites into the cDNA for cloning into the pET-15B expression vector at the NcoI and BamHI sites. The protein was expressed in *E. coli*. Due to the poor solubility of the expressed full-length protein (Met 1-Gln 422), an N-terminally truncated protein starting at Ser residue at position 40 (Ser 40) was produced. This truncation corresponds to Ser 2 of JNK1 and JNK2 proteins, and is preceded by a methionine (initiation) and a glycine residue. The glycine residue was added in order to introduce an NcoI site for cloning into the expression vector. In addition, systematic C-terminal truncations were performed by PCR to identify a construct that give rise to diffraction-quality crystals. One such construct encodes amino acid residues Ser40-Glu402 of JNK3α1 and is preceded by Met and Gly residues.

The construct was prepared by PCR using deoxyoligonucleotides: 5' GCTCTAGAGCTCC ATGGGCAGCAAAAGCAAAGTTGACAA 3' (forward primer with initiation codon underlined)(SEQ ID NO:1) and 5' TAGCGGATCC TCATTCTGAATTCATTACTTCCTTGTA 3' (reverse primer with stop codon underlined)(SEQ ID NO:2) as primers and was confirmed by DNA sequencing. Control experiments indicated that the truncated JNK3 protein had an equivalent kinase activity towards myelin basic protein when activated with an upstream kinase MKK7 in vitro.

E. coli strain BL21 (DE3) (Novagen) was transformed with the JNK3 expression construct and grown at 30° C. in LB supplemented with 100 μg/ml carbenicillin in shaker flasks until the cells were in log phase ($OD_{600}$~0.8). Isopropylthio-β-D-galactosidase (IPTG) was added to a final concentration of 0.8 mM and the cells were harvested 2 hours later by centrifugation.

E. coli cell paste containing JNK3 was resuspended in 10 volumes/g lysis buffer (50 mM HEPES, pH 7.2, containing 10% glycerol (v/v), 100 mM NaCl, 2 mM DTT, 0.1 mM PMSF, 2 μg/ml Pepstatin, 1 μg/ml each of E-64 and Leupeptin). Cells were lysed on ice using a microfluidizer and centrifuged at 100,000× g for 30 min at 4° C. The 100,000× g supernatant was diluted 1:5 with Buffer A (20 mM HEPES, pH 7.0, 10% glycerol (v/v), 2 mM DTT) and purified by SP-Sepharose (Pharmacia) cation-exchange chromatography (column dimensions: 2.6×20 cm) at 4° C. The resin was washed with 5 column volumes of Buffer A, followed by 5 column volumes of Buffer A containing 50 mM NaCl. Bound JNK3 was eluted with a 7.5 column volume linear gradient of 50–300 mM NaCl. JNK3 eluted between 150–200 mM NaCl.

EXAMPLE 39

Activation of JNK3

5 mg of JNK3 was diluted to 0.5 mg/ml in 50 mM HEPES buffer, pH 7.5, containing 100 mM NaCl, 5 mM DTT, 20 mM $MgCl_2$ and 1 mM ATP. GST-MKK7(DD) was added at a molar ratio of 1:2.5 GST-MKK7:JNK3. After incubation for 30 minutes at 25° C., the reaction mixture was concentrated 5-fold by ultrafiltration in a Centriprep-30 (Amicon, Beverly, Mass.), diluted to 10 ml and an additional 1 mM ATP added. This procedure was repeated three times to remove ADP and replenish ATP. The final addition of ATP was 5 mM and the mixture incubated overnight at 4° C.

The activated JNK3/GST-MKK7(DD) reaction mixture was exchanged into 50 mM HEPES buffer, pH 7.5, containing 5 mM DTT and 5% glycerol (w/v) by dialysis or ultrafiltration. The reaction mixture was adjusted to 1.1 M potassium phosphate, pH 7.5, and purified by hydrophobic interaction chromatography (at 25° C.) using a Rainin Hydropore column. GST-MKK7 and unactivated JNK3 do not bind under these conditions such that when a 1.1 to 0.05 M potassium phosphate gradient is developed over 60 minutes at a flow rate of 1 ml/minute, doubly phosphorylated JNK3 is separated from singly phosphorylated JNK. Activated JNK3 (i.e. doubly phosphorylated JNK3) was stored at −70° C. at 0.25–1 mg/ml.

EXAMPLE 40

JNK Inhibition Assays

Compounds were assayed for the inhibition of JNK3 by a spectrophotometric coupled-enzyme assay. In this assay, a fixed concentration of activated JNK3 (10 nM) was incubated with various concentrations of a potential inhibitor dissolved in DMSO for 10 minutes at 30° C. in a buffer containing 0.1 M HEPES buffer, pH 7.5, containing 10 mM $MgCl_2$, 2.5 mM phosphoenolpyruvate, 200 μM NADH, 150 μg/mL pyruvate kinase, 50 μg/mL lactate dehydrogenase, and 200 μM EGF receptor peptide. The EGF receptor peptide has the sequence KRELVEPLTPSGEAPNQALLR, and is a phosphoryl acceptor in the JNK3-catalyzed kinase reaction. The reaction was initiated by the addition of 10 μM ATP and the assay plate is inserted into the spectrophotometer's assay plate compartment that was maintained at 30° C. The decrease of absorbance at 340 nm was monitored as a function of time. The rate data as a function of inhibitor concentration was fitted to competitive inhibition kinetic model to determine the $K_i$.

For selected compounds of this invention, activity in the JNK inhibition assay is shown in Table 8. Compounds having a $K_i$ less than 0.1 micromolar (μM) are rated "A", compounds having a $K_i$ between 0.1 and 1 μM are rated "B" and compounds having a $K_i$ greater than 1 μM are rated "C".

TABLE 8

Activity in the JNK3 Inhibition Assay.

| No. | Activity | No. | Activity | No. | Activity |
|---|---|---|---|---|---|
| IIA-1 | A | IIA-2 | — | IIA-3 | A |
| IIA-4 | — | IIA-5 | A | IIA-6 | A |
| IIA-7 | A | IIA-8 | A/B | IIA-9 | B |
| IIA-10 | B | IIA-11 | A | IIA-12 | B/C |
| IIA-13 | C | IIA-14 | B | IIA-15 | B |
| IIA-16 | — | IIA-17 | — | IIA-18 | — |
| IIA-19 | — | IIA-20 | — | IIA-21 | — |
| IIA-22 | — | IIA-23 | — | IIA-24 | — |
| IIA-25 | — | IIA-26 | — | IIA-27 | — |
| IIA-28 | — | IIA-29 | — | IIA-30 | — |
| IIA-31 | — | IIA-32 | A | IIA-33 | A |
| IIA-34 | A | IIA-35 | A | IIA-36 | A |
| IIA-37 | A | IIA-38 | A | IIA-39 | A |
| IIA-40 | A | IIA-41 | A | IIA-42 | A |
| IIA-43 | A | IIA-44 | A | IIA-45 | A |
| IIA-46 | A | IIA-47 | A | IIA-48 | A |
| IIA-49 | A | IIA-50 | A | IIA-51 | A |
| IIA-52 | A | IIA-53 | A | IIA-54 | A |
| IIA-55 | A | IIA-56 | A | IIA-57 | A |
| IIA-58 | A | IIA-59 | A | IIA-60 | A |
| IIA-61 | A | IIA-62 | A | IIA-63 | A |
| IIA-64 | A | IIA-65 | A | IIA-66 | A |
| IIA-67 | A | IIA-68 | A | IIA-69 | A |
| IIA-70 | A/B | IIA-71 | A/B | IIA-72 | A/B |
| IIA-73 | B | IIA-74 | B | IIA-75 | B |
| IIA-76 | B | IIA-77 | B | IIA-78 | B |
| IIA-79 | B | IIA-80 | B | IIA-81 | B |
| IIA-82 | B | IIA-83 | B | IIA-84 | B |
| IIA-85 | C | IIA-86 | C | IIA-87 | C |
| IIA-88 | — | IIA-89 | — | IIA-90 | A |
| IIA-91 | A | IIA-92 | A | IIA-93 | A |
| IIA-94 | A | IIA-95 | A | IIA-96 | A |
| IIA-97 | A | IIA-98 | A | IIA-99 | A |
| IIA-100 | A | IIA-101 | A | IIA-102 | A |
| IIA-103 | A | IIA-104 | A | IIA-105 | A |
| IIA-106 | B | IIA-107 | C | IIA-108 | A |
| IIA-109 | A | IIA-110 | C | IIA-111 | C |
| IIA-112 | C | IIA-113 | B | IIA-114 | B |

TABLE 8-continued

Activity in the JNK3 Inhibition Assay.

| No. | Activity | No. | Activity | No. | Activity |
|---|---|---|---|---|---|
| IIA-115 | B | IIA-116 | C | IIA-117 | B |
| IIA-118 | B | IIA-119 | B | IIA-120 | B |
| IIA-121 | C | IIA-122 | B | IIA-123 | B |
| IIA-124 | B | IIA-125 | B | IIA-126 | B |
| IIA-127 | B | IIA-128 | B | IIA-129 | B |
| IIA-130 | A | IIA-131 | A | IIA-132 | A |
| IIA-133 | A | IIA-134 | A | IIA-135 | B |
| IIA-136 | — | IIA-137 | — | IIA-138 | — |
| IIAA-1 | — | IIAA-2 | — | IIAA-3 | — |
| IIAA-4 | B | IIAA-5 | — | IIAA-6 | — |
| IIAA-7 | — | IIAA-8 | — | IIAA-9 | — |
| IIAA-10 | A | IIAA-11 | A | IIAA-12 | A |
| IIAA-13 | A | IIAA-14 | A | IIAA-15 | B |
| IIAA-16 | A | IIAA-17 | C | IIAA-18 | B |
| IIAA-19 | A | IIAA-20 | B | IIAA-21 | B |
| IIAA-22 | B | IIAA-23 | B | IIAA-24 | A |
| IIAA-25 | A | IIAA-26 | C | IIAA-27 | B |
| IIAA-28 | C | IIAA-29 | B | IIAA-30 | C |
| IIAA-31 | A | IIAA-32 | B | IIAA-33 | A |
| IIAA-34 | A | IIAA-35 | A | IIAA-36 | A |
| IIAA-37 | A | IIAA-38 | A | IIAA-39 | B |
| IIIA-1 | B | IIIA-2 | C | IIIA-3 | B |
| IIIA-4 | C | IIIA-5 | C | IIIA-6 | B |
| IIIA-7 | B | IIIA-8 | B | IIIA-9 | C |
| IIIA-10 | C | IIIA-11 | B | IIIA-12 | B |
| IIIA-13 | — | IIIA-14 | B | IIIA-15 | A |
| IIIA-16 | — | IIIA-17 | — | IIIA-18 | B |
| IIIA-19 | B | IIIA-20 | B | IIIA-21 | B |
| IIIA-22 | C | IIIA-23 | C | IIIA-24 | C |
| IIIA-25 | C | IIIA-26 | C | IIIA-27 | C |
| IIIA-28 | C | IIIA-29 | C | IIIA-30 | B |
| IIIA-31 | B | IIIA-32 | B | IIIA-33 | B |
| IIIA-34 | C | IIIA-35 | C | IIIA-36 | C |
| IIIA-37 | C | IIIA-38 | C | IIIA-39 | C |
| IIIA-40 | C | IIIA-41 | C | IIIA-42 | B |
| IIIA-43 | A | IIIA-44 | B | IIIA-45 | B |
| IIIA-46 | B | IIIA-47 | B | IIIA-48 | B |
| IIIA-49 | B | IIIA-50 | B | IIIA-51 | B |
| IIIA-52 | B | IIIA-53 | B | IIIA-54 | B |
| IIIA-55 | B | IIIA-56 | B | IIIA-57 | B |
| IIIA-58 | B | IIIA-59 | B | IIIA-60 | B |
| IIIA-61 | B | IIIA-62 | B | IIIA-63 | B |
| IIIA-64 | B | IIIA-65 | B | IIIA-66 | B |
| IIIA-67 | B | IIIA-68 | B | IIIA-69 | B |
| IIIA-70 | B | IIIA-71 | B | IIIA-72 | B |
| IIIA-73 | B | IIIA-74 | A | IIIA-75 | B |
| IIIA-76 | — | IIIA-77 | — | IIIA-78 | — |
| IIIA-79 | — | IIIA-80 | — | IIIA-81 | — |
| IIIA-82 | — | IIIA-83 | — | IIIA-84 | — |
| IIIA-85 | — | IIIA-86 | — | IIIA-87 | — |
| IIIA-88 | — | IIIA-89 | — | IIIA-90 | — |
| IIIA-91 | — | IIIA-92 | — | IIIA-93 | — |
| IIIA-94 | — | IIIA-95 | — | IIIA-96 | — |
| IIIA-97 | — | | | | |
| XA-1 | B | XA-2 | C | XA-3 | B |
| XA-4 | B | XA-5 | B | XA-6 | — |
| XIA-1 | — | XIA-2 | — | XIA-3 | — |
| XIA-4 | — | XIA-5 | — | XIA-6 | — |
| XIA-7 | — | XIA-8 | — | XIA-9 | — |
| XIA-10 | — | XIA-11 | — | XIA-12 | — |
| XIA-13 | — | XIA-14 | — | XIA-15 | — |
| XIA-16 | — | XIA-17 | — | XIA-18 | — |
| XIA-19 | — | XIA-20 | — | XIA-21 | — |
| XIA-22 | — | XIA-23 | — | XIA-24 | — |
| XIA-25 | — | XIA-26 | — | XIA-27 | — |
| XIA-28 | — | XIA-29 | — | XIA-30 | — |
| XIA-31 | — | XIA-32 | — | XIA-33 | — |
| XIA-34 | — | XIA-35 | — | XIA-36 | — |
| XIA-37 | — | XIA-38 | — | XIA-39 | — |
| XIA-40 | — | XIA-41 | — | XIA-42 | — |
| XIA-43 | — | XIA-44 | — | XIA-45 | A |
| XIA-46 | A | XIA-47 | A | XIA-48 | A |
| XIA-49 | A | XIA-50 | A | XIA-51 | A |
| XIA-52 | A | XIA-53 | A | | |

EXAMPLE 41

Src Inhibition Assays

The compounds were assayed as inhibitors of full length recombinant human Src kinase (from Upstate Biotechnology, cat. no. 14-117) expressed and purified from baculo viral cells. Src kinase activity was monitored by following the incorporation of $^{33}P$ from ATP into the tyrosine of a random poly Glu-Tyr polymer substrate of composition, Glu:Tyr 4:1 (Sigma, cat. no. P-0275). The following were the final concentrations of the assay components: 0.05 M HEPES, pH 7.6, 10 mM $MgCl_2$, 2 mM DTT, 0.25 mg/ml BSA, 10 μM ATP (1–2 μCi $^{33}P$-ATP per reaction), 5 mg/ml poly Glu-Tyr, and 1–2 units of recombinant human Src kinase. In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 min before initiating the reaction with $^{33}P$-ATP. After 20 min of reaction, the reactions were quenched with 150 μl of 10% trichloroacetic acid (TCA) containing 20 mM $Na_3PO_4$. The quenched samples were then transferred to a 96-well filter plate (Whatman, UNI-Filter GF/F Glass Fiber Filter, cat no. 7700-3310) installed on a filter plate vacuum manifold. Filter plates were washed four times with 10% TCA containing 20 mM $Na_3PO_4$ and then 4 times with methanol. 200 μl of scintillation fluid was then added to each well. The plates were sealed and the amount of radioactivity associated with the filters was quantified on a TopCount scintillation counter.

The most active compounds in the Src assay were found to be those compounds of formula I where G is an optionally substituted aryl and $R^1$ is $Ar^2$.

EXAMPLE 42

Lck Inhibition Assays

The compounds were assayed as inhibitors of lck kinase purified from bovine thymus (from Upstate Biotechnology, cat. no. 14-106). Lck kinase activity was monitored by following the incorporation of $^{33}P$ from ATP into the tyrosine of a random poly Glu-Tyr polymer substrate of composition, Glu:Tyr=4:1 (Sigma, cat. no. P-0275). The following were the final concentrations of the assay components: 0.05 M HEPES, pH 7.6, 10 mM $MgCl_2$, 2 mM DTT, 0.25 mg/ml BSA, 10 μM ATP (1–2 μCi $^{33}P$-ATP per reaction), 5 mg/ml poly Glu-Tyr, and 1–2 units of lck kinase. In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 min before initiating the reaction with $^{33}P$-ATP. After 20 min of reaction, the reactions were quenched with 150 μl of 10% trichloroacetic acid (TCA) containing 20 mM $Na_3PO4$. The quenched samples were then transferred to a 96-well filter plate (Whatman, UNI-Filter GF/F Glass Fiber Filter, cat no. 7700-3310) installed on a filter plate vacuum manifold. Filter plates were washed four times with 10% TCA containing 20 mM $Na_3PO_4$ and then 4 times with methanol. 200 μl of scintillation fluid was then added to each well. The plates were sealed and the amount of radioactivity associated with the filters was quantified on a TopCount scintillation counter.

The most active compounds in the Lck assay were found to be those compounds of formula I where G is an optionally substituted aryl and $R^1$ is $Ar^2$.

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

We claim:

1. A compound having the formula:

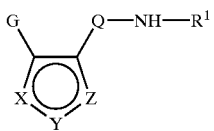

I wherein:

X-Y-Z is selected from one of the following:

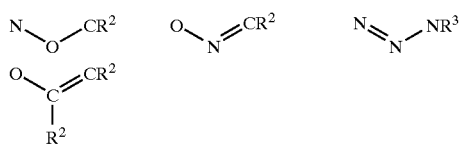

$R^1$ is H, $CONH_2$, $T_{(n)}$—R, or $T_{(n)}$—$Ar^2$;
R is an aliphatic or substituted aliphatic group;
n is zero or one;
T is C(=O), $CO_2$, CONH, $S(O)_2$, $S(O)_2NH$, $COCH_2$ or $CH_2$;
each $R^2$ is independently selected from hydrogen, —R, —$CH_2OR$, —$CH_2OH$, —CH=O, —$CH_2SR$, —$CH_2S$(O)$_2R$, —$CH_2$(C=O)R, —$CH_2CH_2CO_2R$, —$CH_2CO_2H$, —$CH_2CN$, —$CH_2NHR$, —$CH_2N(R)_2$, —H=N—OR, —CH=NNHR, —CH=NN(R)$_2$, —CH=NNHCOR, —CH=NNHCO$_2$R, —CH=NNHSO$_2$R, -aryl, —substituted aryl, —$CH_2$(aryl), —$CH_2$(substituted aryl), —$CH_2NH_2$, —$CH_2NHCOR$, —$CH_2NHCONHR$, —$CH_2NHCON(R)_2$, —$CH_2NRCOR$, —$CH_2NHCO_2R$, —$CH_2CONHR$, —$CH_2CON(R)_2$, —$CH_2SO_2NH_2$, —$CH_2$(heterocyclyl), —$CH_2$(substituted heterocyclyl), —(heterocyclyl), or —(substituted heterocyclyl);
each $R^3$ is independently selected from hydrogen, R, COR, $CO_2R$ or $S(O)_2R$;
C is R or $Ar^1$;
$Ar^1$ is aryl, substituted aryl, aralkyl, substituted aralkyl, heterocyclyl, or substituted heterocyclyl, wherein $Ar^1$ is optionally fused to a partially unsaturated or fully unsaturated five to seven membered ring containing zero to three heteroatoms;
Q—NH is

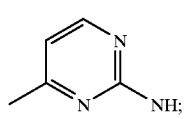

wherein the H of Q—NH is optionally replaced by $R^3$;
$Ar^2$ is aryl, substituted aryl, heterocyclyl or substituted heterocyclyl, wherein $Ar^2$ is optionally fused to a partially unsaturated or fully unsaturated five to seven membered ring containing zero to three heteroatoms;

wherein each substitutable carbon atom in $Ar^2$, including the fused ring when present, is optionally and independently substituted by halo, R, OR, SR, OH, $NO_2$, CN, $NH_2$, NHR, $N(R)_2$, NHCOR, NHCONHR, NHCON(R)$_2$, NRCOR, NHCO$_2$R, $CO_2R$, $CO_2H$, COR, CONHR, CON(R)$_2$, $S(O)_2R$, $SONH_2$, S(O)R, $SO_2NHR$, or NHS(O)$_2R$, and wherein each saturated carbon in the fused ring is further optionally and independently substituted by =O, =S, =NNHR, =NNR$_2$, =N—OR, =NNHCOR, =NNHCO$_2$R, =NNHSO$_2$R, or =NR; and wherein each substitutable nitrogen atom in $Ar^2$ is optionally substituted by R, COR, $S(O)_2R$, or $CO_2R$;

provided that:
when compound of formula I is:

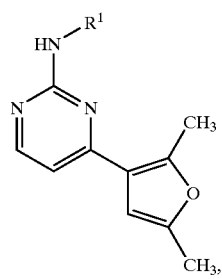

then $R^1$ is not phenyl, 3-$OCH_3$-phenyl, 3-$CH_3$-phenyl, 4-N($CH_3$)$_2$-phenyl, 4-N($CH_2CH_3$)$_2$-phenyl, 4-Et-phenyl, 3,5-($CH_3$)$_2$-phenyl, or 3-N($CH_3$)$_2$-phenyl.

2. The compound of claim 1, where G is $Ar^1$.

3. The compound of claim 2, having the formula

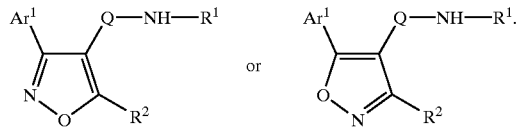

4. The compound of claim 3, where $R^1$ is alkoxyalkyl, alkoxycarbonylalkyl, hydroxyalkyl, pyridinylalkyl, alkoxycycloalkyl, cycloalkyl, alkoxycarbonylcycloalkyl, hydroxycycloalkyl, $Ar^2$ or T-$Ar^2$ where T is C(=O).

5. The compound of claim 4, where $R^1$ is cyclohexyl, cyclohexanol-4-yl, cyclohexanon-4-yl, 2-propan-1-ol, 2-methoxy-1-methylethyl, 3-butyryl alkyl ester, 2-pyridinyl-2-ethyl, or an optionally substituted phenyl, naphthyl, pyridyl, quinolinyl, thienyl or indanyl.

6. The compound of claim 5, where $R^2$ is an optionally substituted alkyl.

7. A compound selected from one of the following compounds:
a) compounds having the general formula IIA:

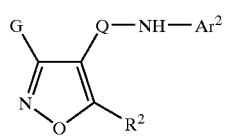

IIA where Q is:

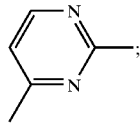

Ar² is

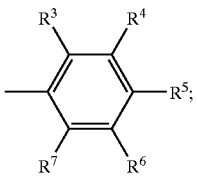

and further defined as follows:

| No. | G | R² | R³ | R⁴ | R⁵ | R⁶ | R⁷ |
|---|---|---|---|---|---|---|---|
| IIA-1 | Ph | Me | H | H | H | H | H |
| IIA-2 | Ph | Me | H | H | OMe | H | H |
| IIA-3 | Ph | Me | H | OMe | OMe | H | H |
| IIA-4 | Ph | Me | Me | H | H | H | H |
| IIA-5 | Ph | Me | Me | H | CONH₂ | H | H |
| IIA-6 | Ph | Me | Me | H | CN | H | H |
| IIA-7 | Ph | Me | H | CN | H | H | H |
| IIA-8 | Ph | Me | Me | F | H | H | H |
| IIA-9 | Ph | Me | Me | H | F | H | H |
| IIA-10 | Ph | Me | CF₃ | H | H | H | H |
| IIA-11 | 4-F-Ph | Me | H | H | H | H | H |
| IIA-12 | 2,3-(MeO)₂-Ph | Me | H | H | H | H | H |
| IIA-13 | 2,4-(MeO)₂-Ph | Me | H | H | H | H | H |
| IIA-14 | 2-Cl-Ph | Me | H | H | H | H | H |
| IIA-15 | 3,4-Cl₂-Ph | Me | H | H | H | H | H |
| IIA-22 | Et | Me | H | H | H | H | H |
| IIA-23 | PhCH₂OCH₂— | Me | H | H | H | H | H |
| IIA-25 | 3-F-Ph | Me | H | CN | H | H | H |
| IIA-26 | 3-F-Ph | Me | H | H | CN | H | H |
| IIA-27 | 3-F-Ph | Me | H | F | H | H | H |
| IIA-28 | 3-F-Ph | Me | H | H | F | H | H |
| IIA-29 | 3-F-Ph | Me | H | Me | CN | H | H |
| IIA-30 | 3-F-Ph | Me | H | F | CN | H | H |
| IIA-31 | 3-F-Ph | Me | H | H | SMe | H | H |
| IIA-32 | Ph | Me | H | F | CN | H | H |
| IIA-33 | Ph | Me | H | F | H | H | H |
| IIA-34 | Ph | Me | H | H | CN | H | H |
| IIA-35 | Ph | Me | H | H | COMe | H | H |
| IIA-36 | Ph | Me | H | CH=CH | H | H | H |
| IIA-37 | Ph | Me | H | SMe | H | H | H |
| IIA-38 | Ph | Me | H | Me | CN | H | H |
| IIA-39 | Ph | Me | H | COMe | H | H | H |
| IIA-41 | Ph | Me | OMe | H | H | H | H |
| IIA-42 | Ph | Me | H | H | F | H | H |
| IIA-44 | Ph | Me | H | H | Ph | H | H |
| IIA-45 | Ph | Me | H | Me | H | Me | H |
| IIA-46 | Ph | Me | H | H | SMe | H | H |
| IIA-49 | Ph | Me | OMe | H | H | CN | H |
| IIA-51 | Ph | Me | F | H | H | CN | H |
| IIA-54 | Ph | Me | Me | H | CN | H | H |
| IIA-55 | 2-F-Ph | Me | H | H | H | H | H |
| IIA-56 | Ph | Me | F | H | F | H | H |
| IIA-57 | Ph | Me | Me | H | CONH₂ | H | H |
| IIA-58 | Ph | Me | Me | Cl | H | H | H |
| IIA-59 | Ph | Me | F | H | H | H | H |
| IIA-60 | 2,6-F₂-Ph | Me | H | H | H | H | H |
| IIA-61 | Ph | Me | Me | H | OMe | H | H |
| IIA-62 | Ph | Me | OMe | H | H | H | H |
| IIA-63 | Ph | Me | H | H | SO₂Me | H | H |
| IIA-65 | Ph | Me | NO₂ | H | H | H | H |
| IIA-66 | 3-F-Ph | Me | H | H | H | H | H |
| IIA-69 | Ph | Me | CH:CH | H | H | H | H |
| IIA-70 | Ph | Me | Me | F | H | H | H |
| IIA-71 | Ph | Me | Cl | H | H | OMe | H |
| IIA-72 | Ph | Me | H | Me | OMe | H | H |
| IIA-73 | Ph | Me | OMe | H | H | OMe | H |
| IIA-74 | 2,5-F₂-Ph | Me | H | H | H | H | H |
| IIA-75 | 2-Cl-6-F-Ph | Me | H | H | H | H | H |
| IIA-76 | 2-Cl-Ph | Me | H | H | H | H | H |
| IIA-77 | 3,4-Cl₂-Ph | Me | H | H | H | H | H |
| IIA-78 | Ph | Me | Me | H | F | H | H |

-continued

| No. | G | R² | R³ | R⁴ | R⁵ | R⁶ | R⁷ |
|---|---|---|---|---|---|---|---|
| IIA-79 | 2-Br-Ph | Me | H | H | H | H | H |
| IIA-80 | 2,3-F₂-Ph | Me | H | H | H | H | H |
| IIA-81 | Ph | Me | SMe | H | H | H | H |
| IIA-82 | 3-CF₃-Ph | Me | H | H | H | H | H |
| IIA-83 | 3,5-F₂-Ph | Me | H | H | H | H | H |
| IIA-84 | 2,6-Cl₂-Ph | Me | H | H | H | H | H |
| IIA-85 | 2,3-(MeO)₂-Ph | Me | H | H | H | H | H |
| IIA-86 | Me | Me | H | H | H | H | H |
| IIA-87 | cyclopropyl | Me | H | H | H | H | H |
| IIA-88 | cyclohexyl | Me | H | H | H | H | H |
| IIA-89 | 2,4-(MeO)₂-Ph | Me | H | H | H | H | H |
| IIA-90 | t-butyl | Me | H | H | H | H | H |
| IIA-91 | 2,6-F₂-Ph | Me | H | H | COMe | H | H |
| IIA-92 | 2,6-F₂-Ph | Me | H | CN | H | H | H |
| IIA-93 | 2,6-F₂-Ph | Me | H | H | CN | H | H |
| IIA-94 | 2,6-F₂-Ph | Me | H | F | H | H | H |
| IIA-95 | 2,6-F₂-Ph | Me | H | H | F | H | H |
| IIA-96 | 2,6-F₂-Ph | Me | H | CN | F | H | H |
| IIA-97 | 2,6-F₂-Ph | Me | H | H | SMe | H | H |
| IIA-102 | Ph | Me | H | Me | H | H | H |
| IIA-103 | Ph | Me | H | H | Me | H | H |
| IIA-104 | 2-Me-Ph | Me | H | H | H | H | H |
| IIA-105 | 2-Me-Ph | Me | H | F | CN | H | H |
| IIA-106 | 2-Me-Ph | Me | H | F | H | H | H |
| IIA-107 | 2-Me-Ph | Me | H | H | CN | H | H |
| IIA-108 | 2-Me-Ph | Me | H | Me | H | H | H |
| IIA-109 | 2-Me-Ph | Me | H | CN | H | H | H |
| IIA-110 | 2-CF₃-Ph | Me | H | F | CN | H | H |
| IIA-111 | 2-CF₃-Ph | Me | H | CN | H | H | H |
| IIA-112 | 2-CF₃-Ph | Me | H | H | H | H | H |
| IIA-113 | 3,4-(OCH₂O)-Ph | Me | H | F | CN | H | H |
| IIA-114 | 3,4-(OCH₂O)-Ph | Me | H | CN | H | H | H |
| IIA-115 | 3,4-(OCH₂O)-Ph | Me | H | H | H | H | H |
| IIA-116 | 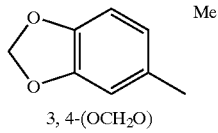 3,4-(OCH₂O) | Me | | 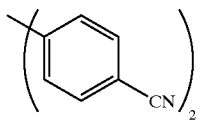 bis-N, N'-4-cyanophenyl | | | |
| IIA-117 | 3-OBn-Ph | Me | H | F | CN | H | H |
| IIA-118 | 3-OBn-Ph | Me | H | CN | H | H | H |
| IIA-119 | 3-OBn-Ph | Me | H | H | H | H | H |
| IIA-120 | 3-NO₂-Ph | Me | H | F | CN | H | H |
| IIA-121 | 3-NO₂-Ph | Me | | bis-N,N'-4-cyanophenyl | | | |
| IIA-122 | 3-NO₂-Ph | Me | H | CN | H | H | H |
| IIA-123 | 3-NO₂-Ph | Me | H | H | H | H | H |
| IIA-124 | 3-CN-Ph | Me | H | F | CN | H | H |
| IIA-125 | 3-CN-Ph | Me | H | H | CN | H | H |
| IIA-126 | 3-CN-Ph | Me | H | CN | H | H | H |
| IIA-127 | 3-CN-Ph | Me | H | H | H | H | H |
| IIA-128 | 3-NO₂-Ph | Me | H | H | CO₂Et | H | H |
| IIA-129 | 3-CN-Ph | Me | H | CO₂Me | H | H | H |
| IIA-130 | Ph | Me | H | CO₂Et | H | H | H |
| IIA-131 | Ph | Me | N | H | NO₂ | H | H | b) compounds having the general formula IIA:

and further defined as follows:

| | No. | G | A | R¹ |
|---|---|---|---|---|
| IIA | IIAA-3 | Ph | N | 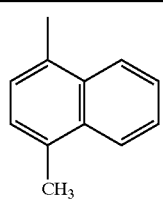 |

-continued
| No. | G | A | R¹ |
|---|---|---|---|
| IIAA-4 | Ph | N | 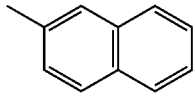 |
| IIAA-5 | Ph | N | 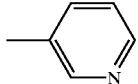 |
| IIAA-6 | Ph | N | 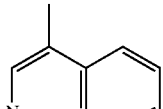 |
| IIAA-7 | Ph | N | 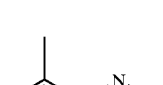 |
| IIAA-8 | Ph | N | 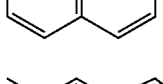 |
| IIAA-9 | 3-F-Ph | N | 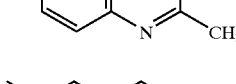 |
| IIAA-10 | Ph | N | 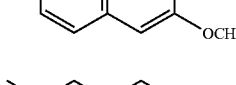 |
| IIAA-11 | Ph | N | 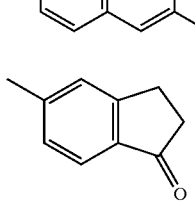 |
| IIAA-12 | Ph | N | 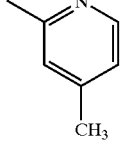 |
| IIAA-13 | Ph | N | 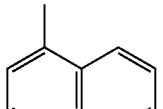 |
| IIAA-14 | 2,6-F₂-Ph | N | 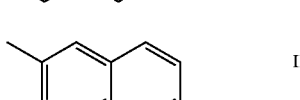 |
-continued
| No. | G | A | R¹ |
|---|---|---|---|
| IIAA-15 | Ph | N | 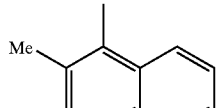 |
| IIAA-17 | Ph | N | 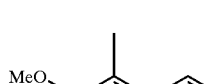 |
| IIAA-18 | Ph | N | 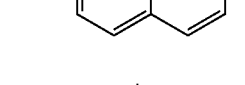 |
| IIAA-19 | 2-Me-Ph | N | 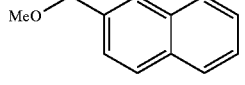 |
| IIAA-20 | 2-Me-Ph | N | 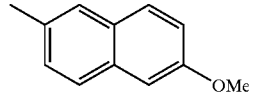 |
| IIAA-21 |  | N | 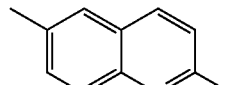 |
| IIAA-22 | 3-NO₂-Ph | N | 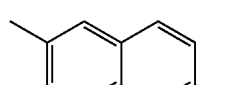 |
| IIAA-23 | 3-CN-Ph | N | 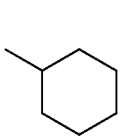 |
| IIAA-24 | Ph | N | 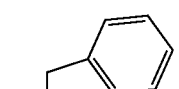 |
| IIAA-25 | Ph | N | 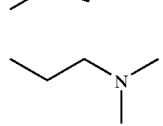 |
| IIAA-26 | Ph | N |  |

-continued

| No. | G | A | R¹ |
|---|---|---|---|
| IIAA-27 | Ph | N | 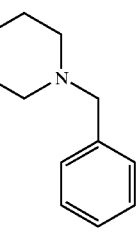 |
| IIAA-28 | Ph | N | 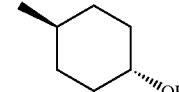 |
| IIAA-29 | Ph | N | 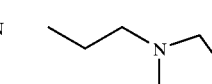 |
| IIAA-30 | Ph | N | 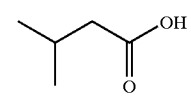 |
| IIAA-31 | Ph | N | 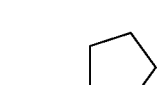 |
| IIAA-32 | Ph | N | 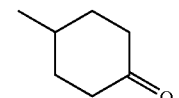 |
| IIAA-33 | Ph | N | 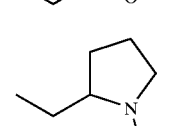 |
| IIAA-34 | Ph | N | 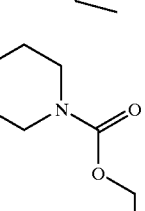 |
| IIAA-35 | Ph | N | 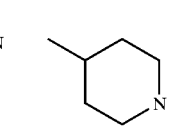 |

-continued

| No. | G | A | R¹ |
|---|---|---|---|
| IIAA-36 | Ph | N | 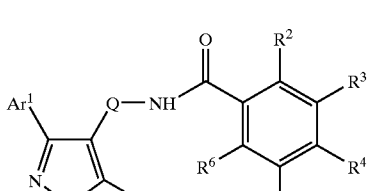 |
| IIAA-37 | Ph | N |  |
| IIAA-38 | Ph | N | 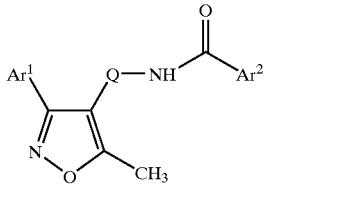 | c) compounds having the one of the general formulas:

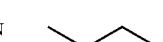

IIIA

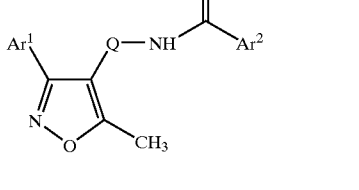

or

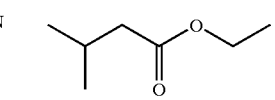

wherein Q is

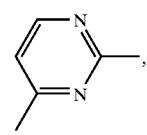

and further defined as follows:

| No. | Ar¹ | R² | R³ | R⁴ | R⁵ | R⁶ |
|---|---|---|---|---|---|---|
| IIIA-1 | phenyl | H | H | H | H | H |
| IIIA-2 | phenyl | Br | H | H | H | H |
| IIIA-3 | phenyl | F | H | H | H | H |
| IIIA-4 | phenyl | Cl | H | H | H | H |
| IIIA-5 | phenyl | $CH_3$ | H | H | H | H |
| IIIA-6 | phenyl | H | $CH_3$ | H | H | H |
| IIIA-7 | phenyl | H | H | $OCH_3$ | H | H |
| IIIA-8 | phenyl | H | $OCH_3$ | $OCH_3$ | H | H |

-continued

| No. | Ar¹ | R² | R³ | R⁴ | R⁵ | R⁶ |
|---|---|---|---|---|---|---|
| IIIA-9 | phenyl | OCH₃ | H | OCH₃ | H | H |
| IIIA-10 | phenyl | OCH₃ | H | H | H | OCH₃ |
| IIIA-11 | phenyl | H | H | CN | H | H |
| IIIA-12 | 5-fluorophenyl | H | H | OCH₃ | H | H |
| IIIA-13 | phenyl | H | OCH₃ | OCH₃ | OCH₃ | H |
| IIIA-14 | phenyl | H | H | F | H | H |
| IIIA-15 | phenyl | colspan=5 | Ar² is 2-thienyl | | | |
| IIIA-16 | phenyl | colspan=5 | Ar² is 1-oxo-indan-5-yl | | | |
| IIIA-17 | phenyl | colspan=5 | Ar² is 4-pyridyl | | | |
| IIIA-18 | 2-CH₃-phenyl | H | OCH₃ | OCH₃ | OCH₃ | H |
| IIIA-19 | 2-CH₃-phenyl | H | OCH₃ | H | H | H |
| IIIA-20 | 2-CH₃-phenyl | H | H | OCH₃ | H | H |
| IIIA-21 | 2-CH₃-phenyl | H | OCH₃ | H | OCH₃ | H |
| IIIA-22 | 2-CF₃-phenyl | H | OCH₃ | OCH₃ | OCH₃ | H |
| IIIA-23 | 2-CF₃-phenyl | H | OCH₃ | H | H | H |
| IIIA-24 | 2-CF₃-phenyl | H | H | OCH₃ | H | H |
| IIIA-25 | 2-CF₃-phenyl | H | OCH₃ | H | OCH₃ | H |
| IIIA-26 | benzo[3,5]dioxole | H | OCH₃ | OCH₃ | OCH₃ | H |
| IIIA-27 | benzo[3,5]dioxole | H | OCH₃ | H | H | H |
| IIIA-28 | benzo[3,5]dioxole | H | H | OCH₃ | H | H |
| IIIA-29 | benzo[3,5]dioxole | H | OCH₃ | H | OCH₃ | H |
| IIIA-30 | 3-benzyloxy-phenyl | H | OCH₃ | OCH₃ | OCH₃ | H |
| IIIA-31 | 3-benzyloxy-phenyl | H | OCH₃ | H | H | H |
| IIIA-32 | 3-benzyloxy-phenyl | H | H | OCH₃ | H | H |
| IIIA-33 | 3-benzyloxy-phenyl | H | OCH₃ | H | OCH₃ | H |
| IIIA-34 | 3-nitrophenyl | H | OCH₃ | OCH₃ | OCH₃ | H |
| IIIA-35 | 3-nitrophenyl | H | OCH₃ | H | H | H |
| IIIA-36 | 3-nitrophenyl | H | H | OCH₃ | H | H |
| IIIA-37 | 3-nitrophenyl | H | OCH₃ | H | OCH₃ | H |
| IIIA-38 | 3-cyanophenyl | H | OCH₃ | OCH₃ | OCH₃ | H |
| IIIA-39 | 3-cyanophenyl | H | OCH₃ | H | H | H |
| IIIA-40 | 3-cyanophenyl | H | H | OCH₃ | H | H |
| IIIA-41 | 3-cyanophenyl | H | OCH₃ | H | OCH₃ | H |
| IIIA-42 | phenyl | H | OCH₃ | H | OCH₃ | H |
| IIIA-43 | phenyl | H | CN | H | H | H |
| IIIA-44 | phenyl | H | H | CO₂Me | H | H |
| IIIA-45 | 3-fluorophenyl | H | Cl | H | H | H |
| IIIA-46 | 3-fluorophenyl | H | OCH₃ | H | H | H |
| IIIA-47 | 3-fluorophenyl | H | OCH₃ | H | OCH₃ | H |
| IIIA-48 | 3-fluorophenyl | H | Me | H | H | H |
| IIIA-49 | 3-fluorophenyl | H | H | F | H | H |
| IIIA-50 | 3-fluorophenyl | H | H | Me | H | H |
| IIIA-51 | 3-fluorophenyl | H | CN | H | H | H |
| IIIA-52 | 3-fluorophenyl | H | OCH₃ | OCH₃ | OCH₃ | H |
| IIIA-53 | 3-fluorophenyl | colspan=5 | Ar² is 2-naphthyl | | | |
| IIIA-54 | 2-fluorophenyl | H | Cl | H | H | H |
| IIIA-55 | 2-fluorophenyl | H | OCH₃ | H | H | H |
| IIIA-56 | 2-fluorophenyl | H | OCH₃ | H | OCH₃ | H |
| IIIA-57 | 2-fluorophenyl | H | Me | H | H | H |
| IIIA-58 | 2-fluorophenyl | H | H | OCH₃ | H | H |
| IIIA-59 | 2-fluorophenyl | H | H | F | H | H |
| IIIA-60 | 2-fluorophenyl | H | H | Me | H | H |
| IIIA-61 | 2-fluorophenyl | H | CN | H | H | H |
| IIIA-62 | 2-fluorophenyl | H | OCH₃ | OCH₃ | OCH₃ | H |
| IIIA-63 | 2-fluorophenyl | colspan=5 | Ar² is 2-naphthyl | | | |
| IIIA-64 | 2,6-F₂-phenyl | H | Cl | H | H | H |
| IIIA-65 | 2,6-F₂-phenyl | H | OCH₃ | H | H | H |
| IIIA-66 | 2,6-F₂-phenyl | H | OCH₃ | H | OCH₃ | H |
| IIIA-67 | 2,6-F₂-phenyl | H | Me | H | H | H |
| IIIA-68 | 2,6-F₂-phenyl | H | H | OCH₃ | H | H |
| IIIA-69 | 2,6-F₂-phenyl | H | H | F | H | H |
| IIIA-70 | 2,6-F₂-phenyl | H | H | Me | H | H |
| IIIA-71 | 2,6-F₂-phenyl | H | CN | H | H | H |
| IIIA-72 | 2,6-F₂-phenyl | H | OCH₃ | OCH₃ | OCH₃ | H |
| IIIA-73 | 2,6-F₂-phenyl | colspan=5 | Ar² is 2-naphthyl | | | |
| IIIA-74 | phenyl | H | NO₂ | H | H | H |
| IIIA-75 | phenyl | H | NHAc | H | H | H |
| IIIA-76 | phenyl | H | COMe | H | H | H | d) compounds having the general formula:

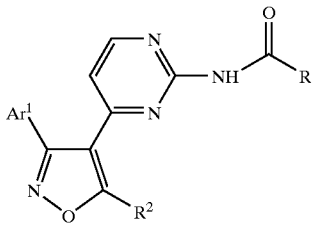

XA wherein $R^2$ is $CH_3$, and further defined as follows:

| No. | $Ar^1$ | R |
|---|---|---|
| XA-1 | phenyl | $CH_3$ |
| XA-2 | 4-F-phenyl | $CH_3$ |
| XA-3 | phenyl | Cyclopentyl |
| XA-4 | phenyl | isobutyl |
| XA-5 | phenyl | propyl | e) compounds having the general formula:

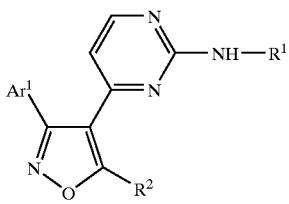

IXA and further defined as follows:

| No. | $Ar^1$ | A | $R^1$ | $R^2$ |
|---|---|---|---|---|
| XIA-13 | phenyl | N | 2-thienoyl | $CH_2Br$ y |
| XIA-14 | phenyl | N | 2-thienoyl | $CH_2$(morpholin-4-yl) |
| XIA-39 | phenyl | N | 2-thienoyl | $CH_2$(piperidin-1-yl) |
| XIA-40 | phenyl | N | 2-thienoyl | $CH_2$(piperazin-1-yl) |
| XIA-42 | 4-F-phenyl | N | 4-cyclohexanol | $CH_2$(morpholin-4-yl) |
| XIA-43 | 4-F-phenyl | N | cyclohexyl | $CH_2OCH_2CH_3$ |
| XIA-44 | 4-F-phenyl | N | cyclohexyl | $CH_2OCH_2$(phenyl) |
| XIA-45 | 4-F-phenyl | N | cyclohexyl | $CH_2OH$ |
| XIA-46 | 4-F-phenyl | N | $CH_2CH_2$(pyridin-2-yl) | $CH_2OH$ |
| XIA-47 | 4-F-phenyl | N | cyclohexyl | $CH_2OCH_3$ |
| XIA-48 | 4-F-phenyl | N | cyclohexyl | $CH_2OCH_2CH_3$ |
| XIA-49 | 4-F-phenyl | N | cyclohexyl | $CH_2OCH_2CH_2OCH_3$ |
| XIA-50 | 4-F-phenyl | N | cyclohexyl | $CH_2O$(tetrahydrofuran-3-yl) |
| XIA-51 | 4-F-phenyl | N | cyclohexyl | 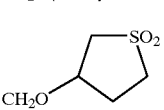 |
| XIA-52 | 4-F-phenyl | N | cyclohexyl | $CH_2OCH_2$(phenyl) |
| XIA-53 | 4-F-phenyl | N | $CH_2CH_2$(pyridin-2-yl) | $CH_2OCH_2$(phenyl) | or f) compounds having one of the structures:

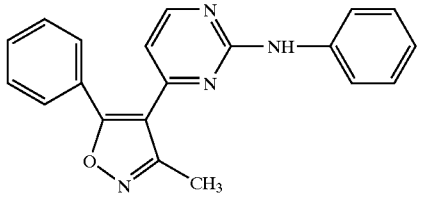

IB-1

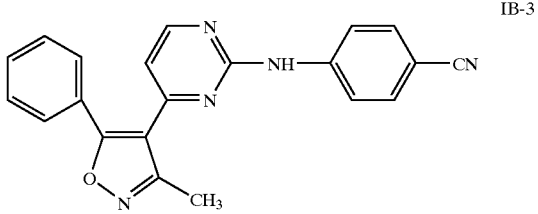

IB-3

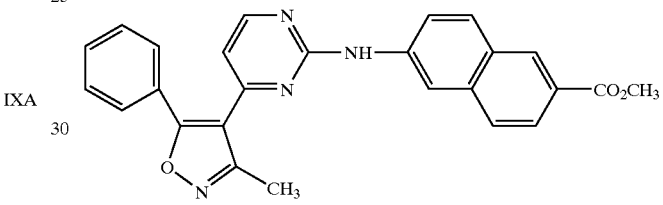

IB-4

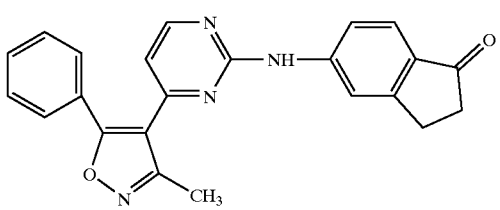

IB-5

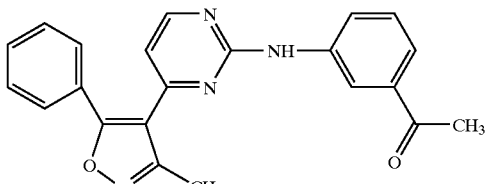

IB-6

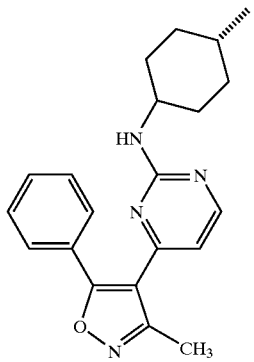

IB-8

-continued
IB-9
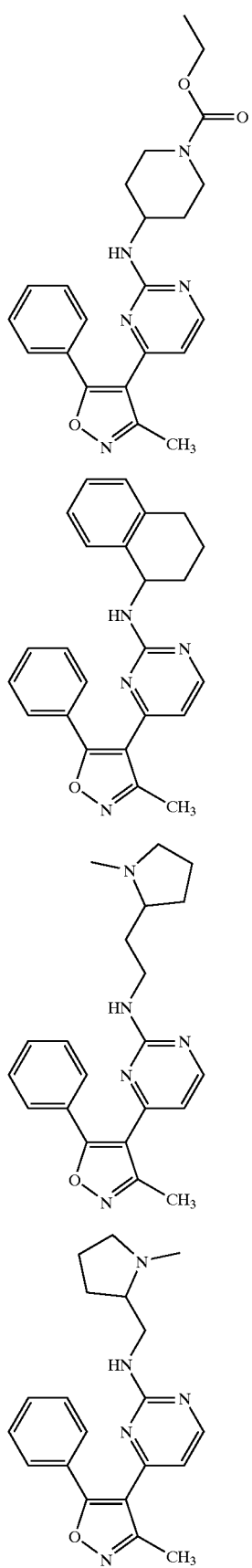
IB-10
IB-11
IB-12
-continued
IB-13
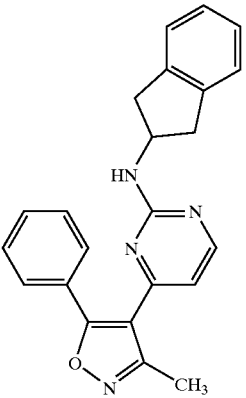
IB-14
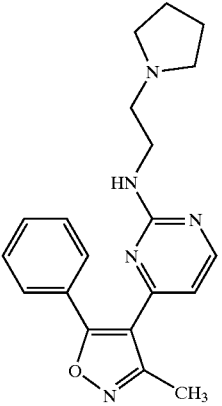
IB-15
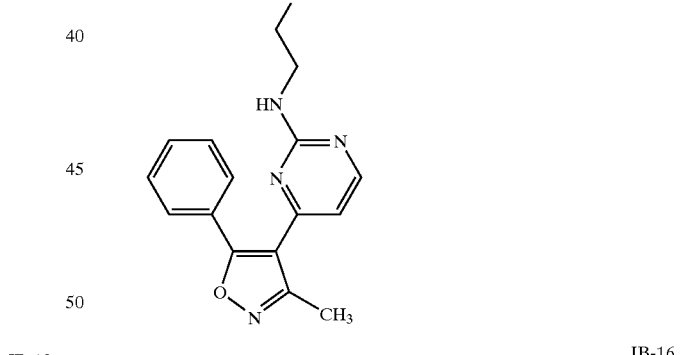
IB-16
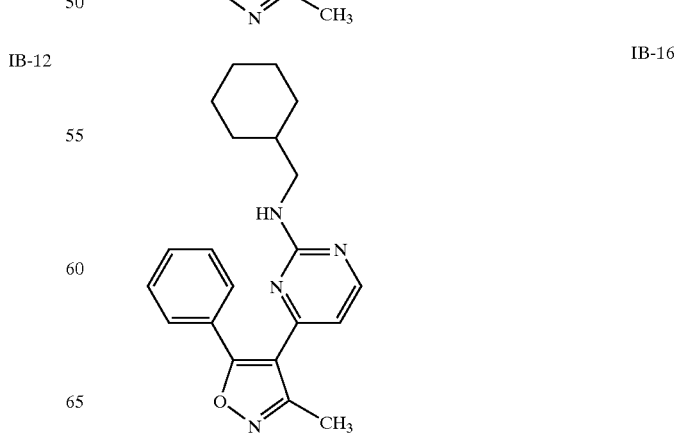

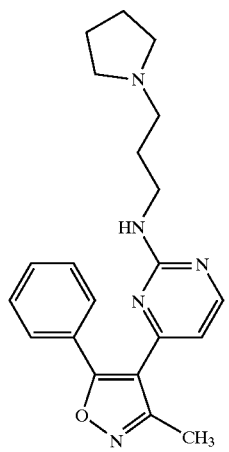
IB-17
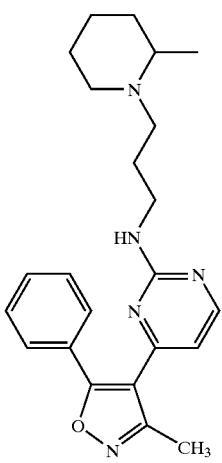
IB-20
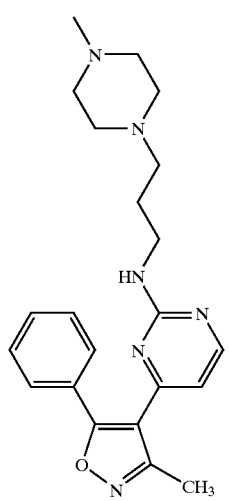
IB-18
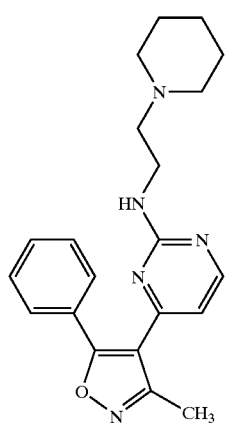
IB-19
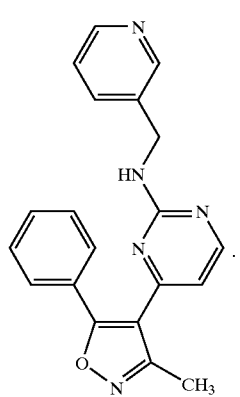
IB-21
IB-22
IB-23

8. A pharmaceutical composition comprising a therapeutically effective amount of a compound of any one of claims 1–7 and a pharmaceutically acceptable carrier.

9. A method of treating a disease selected from inflammatory diseases, rheumatoid arthritis, destructive bone disorders, reperfusion/ischemia in stroke, or cardiac hypertrophy, comprising administering to a mammal in need of such a treatment a therapeutically effective amount of a compound of formula I:

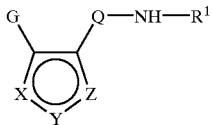

wherein:

X-Y-Z is selected from one of the following:

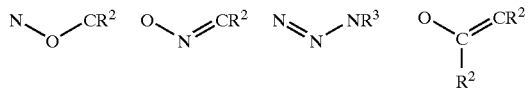

$R^1$ is H, $CONH_2$, $T_{(n)}$-R, or $T_{(n)}$-$Ar^2$

R is an aliphatic or substituted aliphatic group;

n is zero or one;

T is C(=O), $CO_2$, CONH, $S(O)_2$, $S(O)_2NH$, $COCH_2$ or $CH_2$;

each $R^2$ is independently selected from hydrogen, —R, —$CH_2OR$, —$CH_2OH$, —CH=O, —$CH_2SR$, —$CH_2S(O)_2R$, —$CH_2(C=O)R$, —$CH_2CO_2R$, —$CH_2CO_2H$, —$CH_2CN$, —$CH_2NHR$, —$CH_2N(R)_2$, —CH=N—OR, —CH=NNHR, —CH=NN(R)$_2$, —CH=NNHCOR, —CH=NNHCO$_2$R, —CH=NNHSO$_2$R, -aryl, —substituted aryl, —$CH_2$(aryl), —$CH_2$(substituted aryl), —$CH_2NH_2$, —$CH_2NHCOR$, —$CH_2NHCONHR$, —$CH_2NHCON(R)_2$, —$CH_2NRCOR$, —$CH_2NHCO_2R$, —$CH_2CONHR$, —$CH_2CON(R)_2$, —$CH_2SO_2NH_2$, —$CH_2$(heterocyclyl), —$CH_2$(substituted heterocyclyl), —(heterocyclyl), or —(substituted heterocyclyl);

each $R^3$ is independently selected from hydrogen, R, COR, $CO_2R$ or $S(O)_2R$;

G is R or $Ar^1$;

$Ar_1$ is aryl, substituted aryl, aralkyl, substituted aralkyl, heterocyclyl, or substituted heterocyclyl, wherein $Ar_1$ is optionally fused to a partially unsaturated or fully unsaturated five to seven membered ring containing zero to three heteroatoms;

Q—NH is

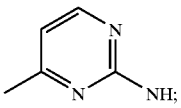

wherein the H of Q—NH is optionally replaced by $R^3$;

$Ar^2$ is aryl, substituted aryl, heterocyclyl or substituted heterocyclyl, wherein $Ar^2$ is optionally fused to a partially unsaturated or fully unsaturated five to seven membered ring containing zero to three heteroatonis;

wherein each substitutable carbon atom in $Ar^2$, including the fused ring when present, is optionally and independently substituted by halo, R, OR, SR, OH, $NO_2$, CN, $NH_2$, NHR, $N(R)_2$, NHCOR, NHCONHR, NHCON(R)$_2$, NRCOR, $NHCO_2R$, $CO_2R$, $CO_2H$, COR, CONHR, CON(R)$_2$, $S(O)_2R$, $SONH_2$, S(O)R, $SO_2NHR$, or $NHS(O)_2R$, and wherein each saturated carbon in the fused ring is further optionally and independently substituted by =O, =S, =NNHR, =$NNR^2$, =N—OR, =NNHCOR, =$NNHCO_2R$, =$NNHSO_2R$, or =NR; and wherein each substitutable nitrogen atom in $Ar_2$ is optionally substituted by R, COR, $S(O)_2R$, or $CO_2R$.

10. The method of claim 9, wherein said method is used to treat:

an inflammatory disease selected from acute pancreatitis, chronic pancreatitis, asthma, allergies, or adult respiratory distress syndrome;

a destructive bone disorder selected from osteoarthritis, osteoporosis or multiple myeloma-related bone disorder;

or is used to treat ischemia/reperfusion in stroke or cardiac hypertrophy.

11. The method of claim 9, wherein said method is used to treat a disease selected from: osteoporosis, osteoarthritis, symptomatic treatment of bone metastasis, rheumatoid arthritis, asthma, ischemic or reperfusion injury, or allergic disease.

* * * * *